(12) United States Patent
Morcuende et al.

(10) Patent No.: US 8,251,938 B1
(45) Date of Patent: Aug. 28, 2012

(54) PROVIDING RELATIVE TRANSLATION WITHOUT ROTATION

(75) Inventors: Jose Morcuende, Iowa City, IA (US); Nicole M. Grosland, Iowa City, IA (US); Kelly Jensen, Long Grove, IA (US); Nicole Jensen, Urbandale, IA (US); Robert Kruse, Sioux Center, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 516 days.

(21) Appl. No.: 12/433,305

(22) Filed: Apr. 30, 2009

(51) Int. Cl.
*A61F 5/14* (2006.01)
*A43B 7/24* (2006.01)
*A61F 5/37* (2006.01)
*A61B 19/00* (2006.01)

(52) U.S. Cl. .................. 602/29; 602/5; 602/16; 602/23; 602/27; 128/846; 128/869; 128/882; 36/140; 36/141; 36/142; 36/143; 36/144

(58) Field of Classification Search .............. 602/5, 23, 602/24, 27–29, 60, 62; 128/846, 869, 882; 36/140, 160
See application file for complete search history.

(56) References Cited

U.S. PATENT DOCUMENTS

| | | | |
|---|---|---|---|
| 2,482,646 A | 9/1949 | Brachman et al. | |
| 2,514,870 A | 7/1950 | Saul | |
| 2,585,342 A | 2/1952 | Morgan | |
| 2,906,261 A | 9/1959 | Craig | |
| 3,487,829 A * | 1/1970 | Barnett | 602/24 |
| 3,892,231 A | 7/1975 | Tummillo | |
| 4,249,523 A | 2/1981 | Bidwell | |
| 4,303,065 A | 12/1981 | Ericson | |
| 4,520,803 A | 6/1985 | Quest | |
| 4,550,722 A | 11/1985 | Kurtz et al. | |
| 4,606,334 A * | 8/1986 | Salmon | 602/24 |
| 7,267,657 B1 | 9/2007 | Mitchell | |
| 7,942,833 B2 * | 5/2011 | Yasuhara | 600/595 |
| 2007/0088240 A1 | 4/2007 | Dobbs | |
| 2007/0142760 A1 | 6/2007 | Mitchell | |

OTHER PUBLICATIONS

Chen et al., J. Ped. Ortho. 27(2007):522-28.
Ponseti et al., Clin. Ortho. Related Res. 451(2006):171-76.
Scher, Curr. Op. Ped. 18(2006):22-25.

* cited by examiner

*Primary Examiner* — Patricia Bianco
*Assistant Examiner* — Brandon L Jackson
(74) *Attorney, Agent, or Firm* — Scott E. Kamholz; Peter K. Sollins; Foley Hoag LLP

(57) ABSTRACT

A device may include a first plate and a second plate, and a linkage system that attaches the first plate and the second plate to one another such that the plates are capable of translating relative to each other, and the plates are incapable of rotating relative to each other.

13 Claims, 46 Drawing Sheets

PROVIDING RELATIVE TRANSLATION WITHOUT ROTATION

SUMMARY

Devices useful for mechanically maintaining the relative orientation of two objects are disclosed. Methods of treating clubfoot are also disclosed.

DETAILED DESCRIPTION

Figure 1:
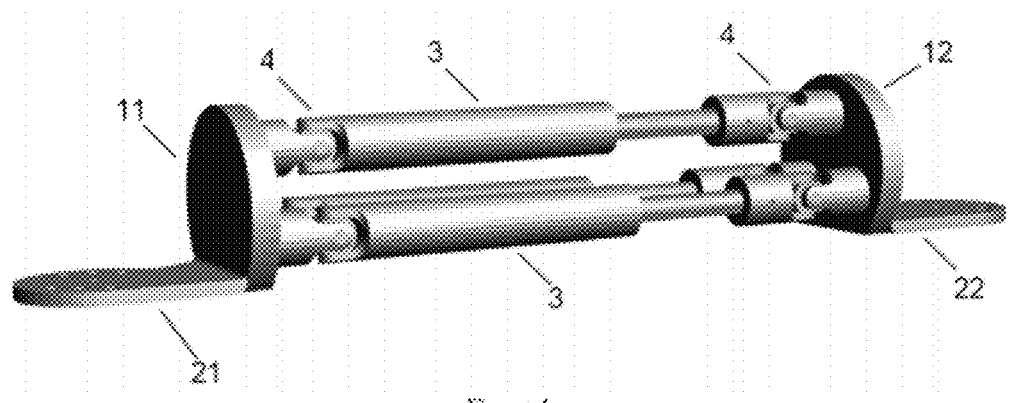
FIG. 1 shows an exemplary embodiment of a device that permits translation of two plates relative to one another but prevents rotation. The device is depicted in its straight or neutral position.
Figure 2A:
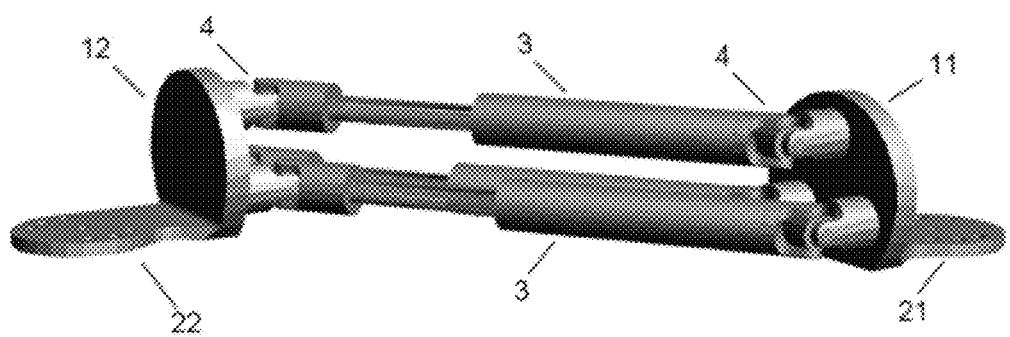
FIG. 2A shows the device in a "shuffle" position, with one platform in front of the other.
Figure 2B:
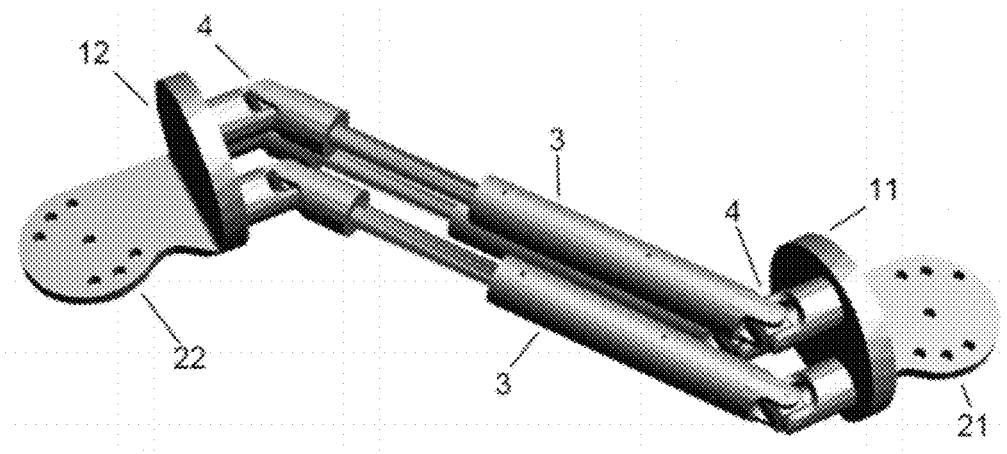
FIG. 2B shows the device in the same "shuffle" position, from above.
Figure 3A:
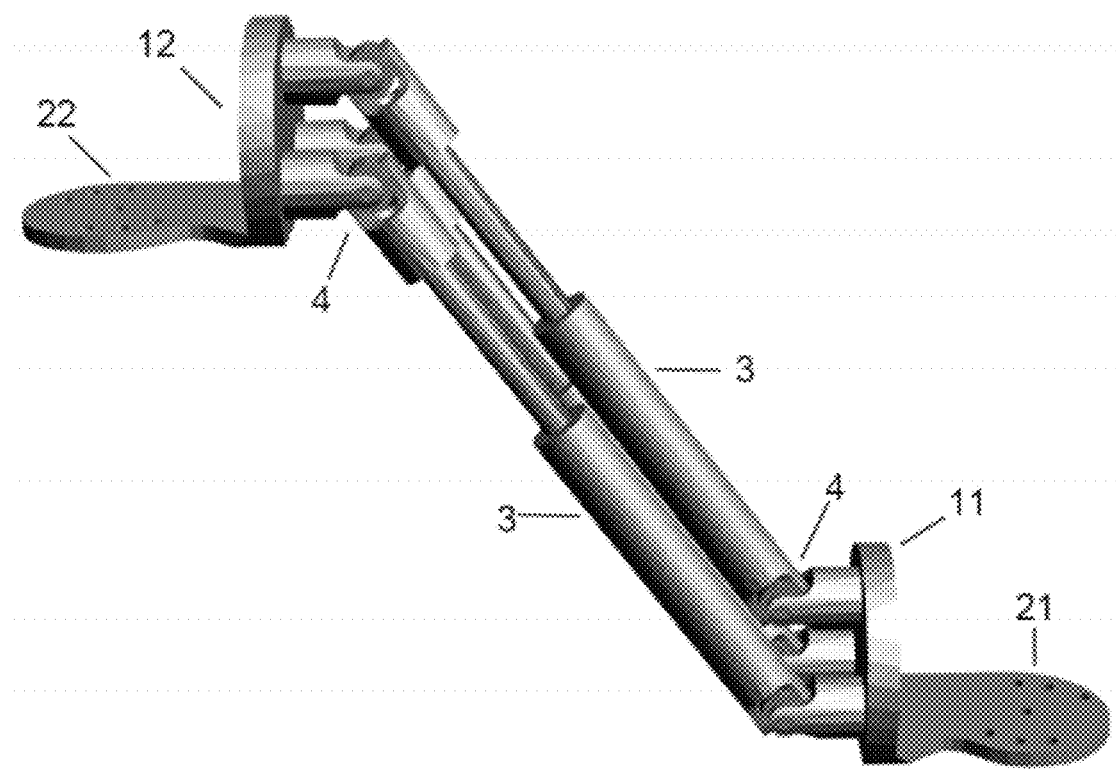
FIG. 3A shows the device in a "marching" position, with one platform above the other.
Figure 3B:
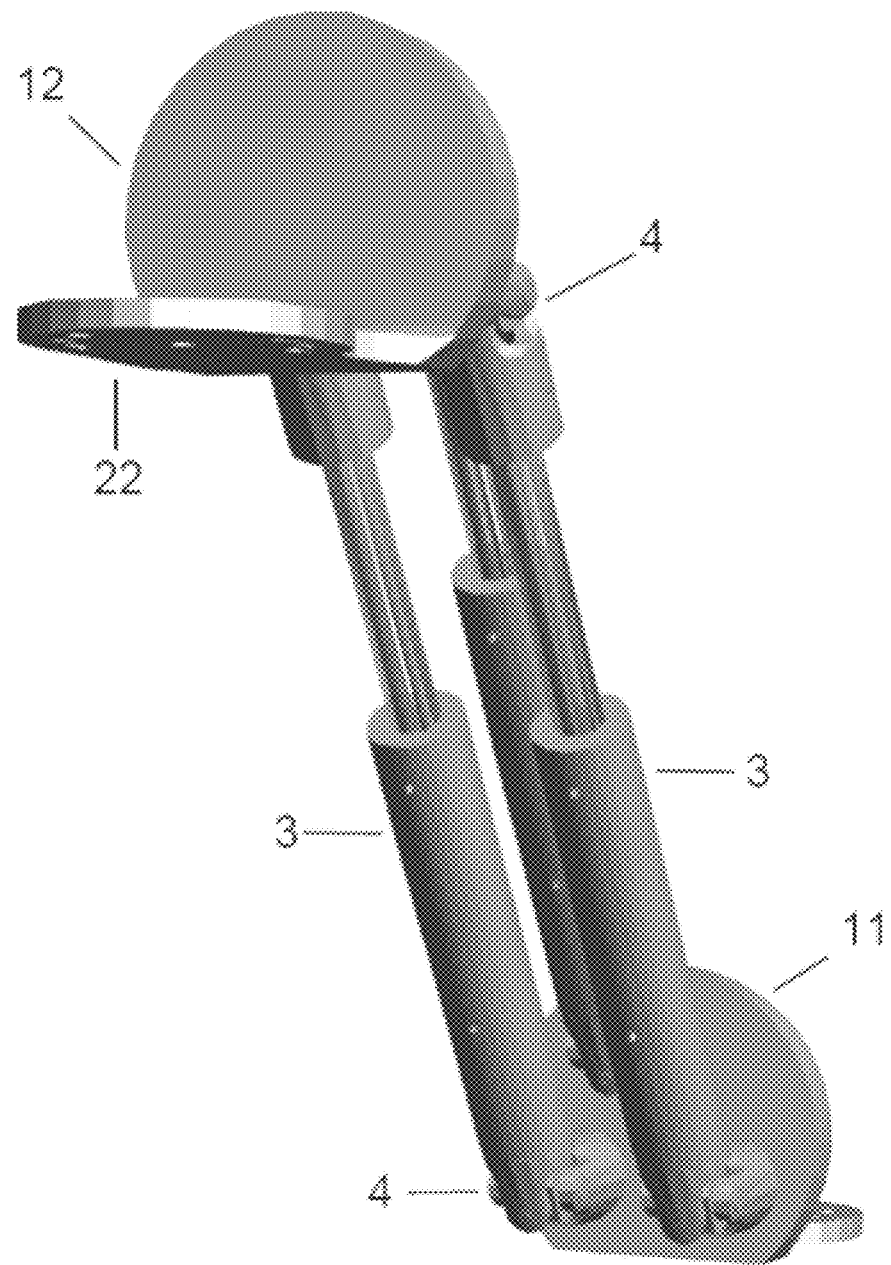
FIG. 3B shows the device in the same "marching" position, from the side.
Figure 4A:
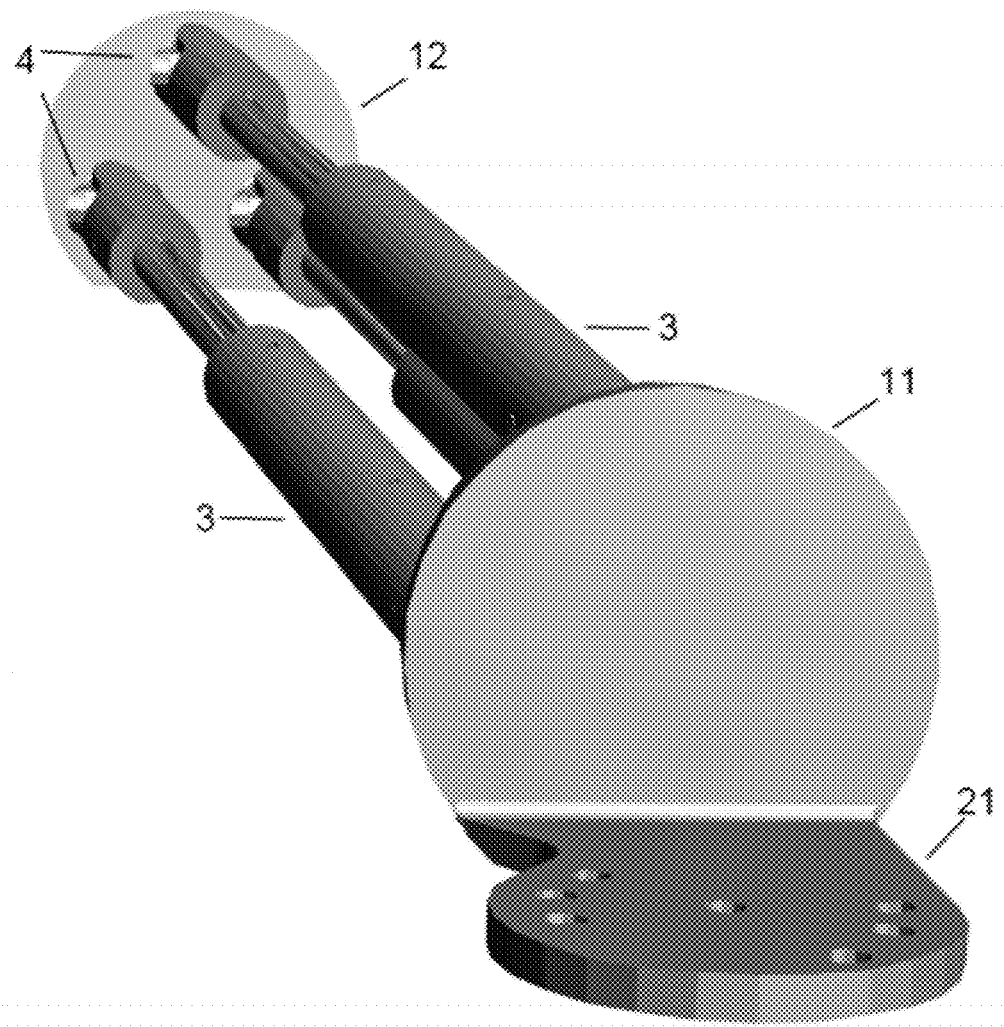
FIG. 4A shows the device in a "walking" position, with one platform both above and in front of the other.
Figure 4B:
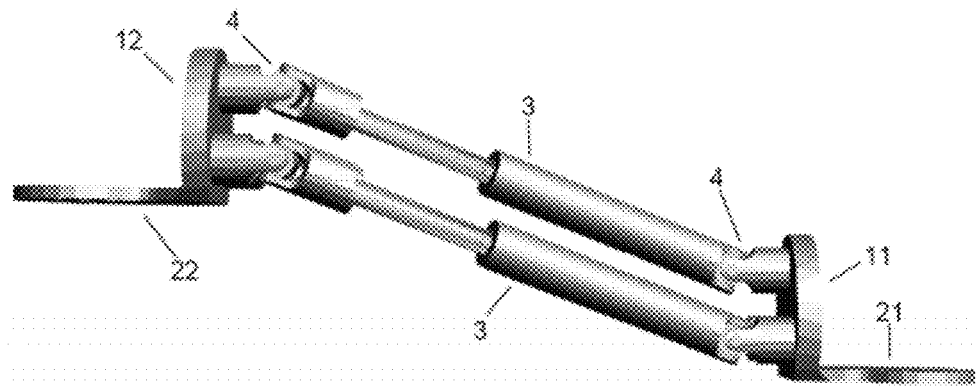
FIG. 4B shows the device in the same "walking" position, from the front.
Figure 4C:
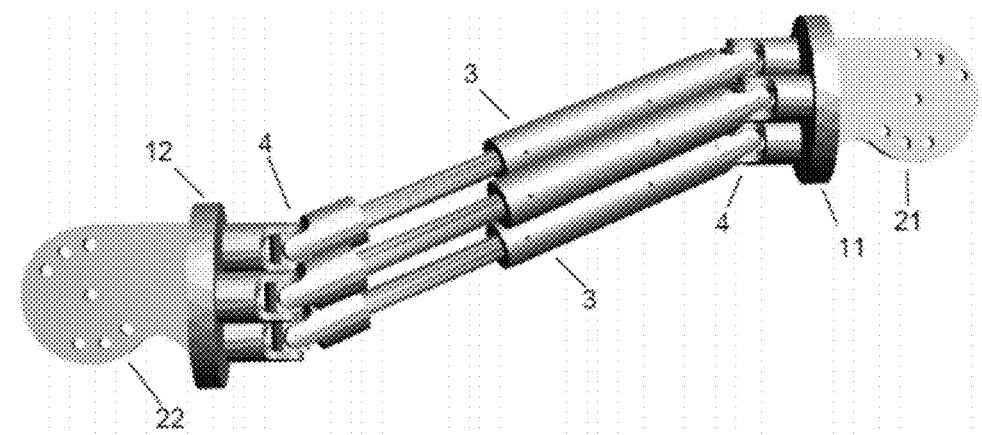
FIG. 4C shows the device in the same "walking" position, from above.

FIG. 1 shows an embodiment of a device useful for treating clubfoot. In the embodiment shown, two vertical plates 11, 12 and two horizontal platforms 21, 22 are disposed at each end of the device. Each plate 11, 12 may be attached to a corresponding platform 21, 22. The plates and platforms may be and are shown integrally formed. The plates 11, 12 and platforms 21, 22 may be substantially planar. In between the plates 11, 12 lie three rods 3. Each of the rods 3 is attached to the first plate 11 at one end and to the second plate 12 at the other end. Each end of each rod is attached to one of the plates by a universal joint 4. The rods are mutually parallel and non-coplanar. The three universal joints attaching the first ends of the rods to the first plate define a first plane. The three universal joints attaching the second ends of the rods to the second plate define a second plane that is parallel to the first plane. The rods and joints collectively form a linkage system that attaches the plates to one another.

The combination of (a) three mutually parallel non-coplanar rods, (b) universal joints attaching those rods at either end to the plates, and (c) the two sets of joints being arranged so that they lie in parallel planes has the remarkable result of permitting relative translation between the plates while preventing relative rotation. A plate may be raised and lowered relative to the other, put forward and backward, and translated through a conic region of space about the other, all without rotating relative to the other plate. That is, the plates can translate relative to one another, but they cannot rotate (i.e., yaw, pitch, or roll) relative to one another. It is not necessary that the plates themselves have any particular shape or be parallel to one another or even to be symmetrically arranged relative to one another, so long as the joints to which the plates attach define parallel planes as discussed above. More than three rods may be used as long as a subset of three rods satisfies the conditions.

This arrangement is useful in a number of applications. In one application, it can be used to make an orthotic for treating clubfoot. In such a "dynamic clubfoot orthotic," a patient's shoes are fixed to and immobilized on the plates. When the patient wears the orthotic, the legs are free to move in the permitted translations but prevented from relative rotation. The shoes (and therefore feet) are angled at a therapeutically beneficial position, and they cannot be rotated from this position while the orthotic is worn. In this context, the dynamic clubfoot orthotic prevents relative dorsi/plantar flexion ("pitch"), adduction/abduction ("yaw"), and inversion/eversion ("roll") of the feet. A similarly-jointed device with all the rods co-planar (including a device with just two parallel rods, which would necessarily be co-planar), would not achieve the desired constraints on relative motion of the plates, because the fully co-planar rods would allow relative rotation of the plates in a plane perpendicular to the plane of the rods.

In the embodiment shown, the rods 3 are adjustable in length. The rods 3 are shown in FIG. 1 as telescoping rods. Regardless of what method of length adjustability is implemented, the rods may also be lockable at a particular length. The rods are typically all the same length; if adjusted, they are adjusted to the same length. An advantage of adjustable rods is the ability to re-size the device as needed (such as with a growing child). If the rods are allowed to have lengths that are different from each other, the device will not maintain the relative parallel orientation of the two plates. Instead, the plates will rotate in a manner precisely determined by the rods' arrangement and length differences. Such an arrangement may be desirable for certain applications in which a limited rotation is appropriate.

Rods may also be provided as monolithic pieces with a set and non-adjustable length. When rods have a set length, there is some point on the first plate that remains at a fixed distance from some point on the other plate in all permitted translations. Advantages of non-adjustable rods include lighter weight and greater device simplicity resulting from having fewer moving parts.

As noted above, one use for each platform 21, 22 is to provide a floor to which a shoe can be attached, either directly or indirectly. However, the device need not include the platforms 21, 22. Even if no platforms are present, a shoe may be attached directly or indirectly to each plate. The shoes may be translationally and rotationally fixed relative to the plates 11, 12.

FIGS. 1, 2, 3 and 4 show various orientations of the device. In FIG. 1, all the joints 4 are straightened. Each platform 21, 22 could have a shoe for a human foot attached to it. If a person were wearing those attached shoes and the wearer of the shoes stood with both feet on the ground and neither foot in front of the other (i.e. both feet even with the coronal plane), then the depicted device would assume the position shown in FIG. 1. Thus FIG. 1 shows the device in a "straightened" or "neutral" position. FIGS. 2A and 2B show the position that the device would take if such a wearer stood with both feet on the ground, but with one foot in front of the other. This is a position that the device would assume if the wearer were shuffling his feet along the ground. FIGS. 3A and 3B show the device in the position it would assume if a wearer were to lift one foot in the air while keeping both feet in the coronal plane, as if the wearer were marching in place. FIGS. 4A, 4B and 4C show the device in the position it would assume if the wearer lifted one foot in the air and put the lifted foot in front of the other, as if the wearer were walking or bicycling.

The four different positions depicted show how the device allows the plates 11, 12 to translate relative to one another while being constrained to a single relative orientation; the same property keeps the rods 3 parallel. No matter how the plates 11, 12 are translated, one in front of the other or one above the other or both, the plates 11, 12 do not rotate relative to each other, and the rods 3 stay parallel. In an actual physical embodiment, minute clearance for articulation in the joints 4 will allow the plates 11, 12 to rotate very slightly relative to one another and the rods 3 to go very slightly out of parallel. This is still considered "parallel," because it substantially maintains the relative orientation of the plates 11, 12 and parallelism of the rods 3.

Figure 5:
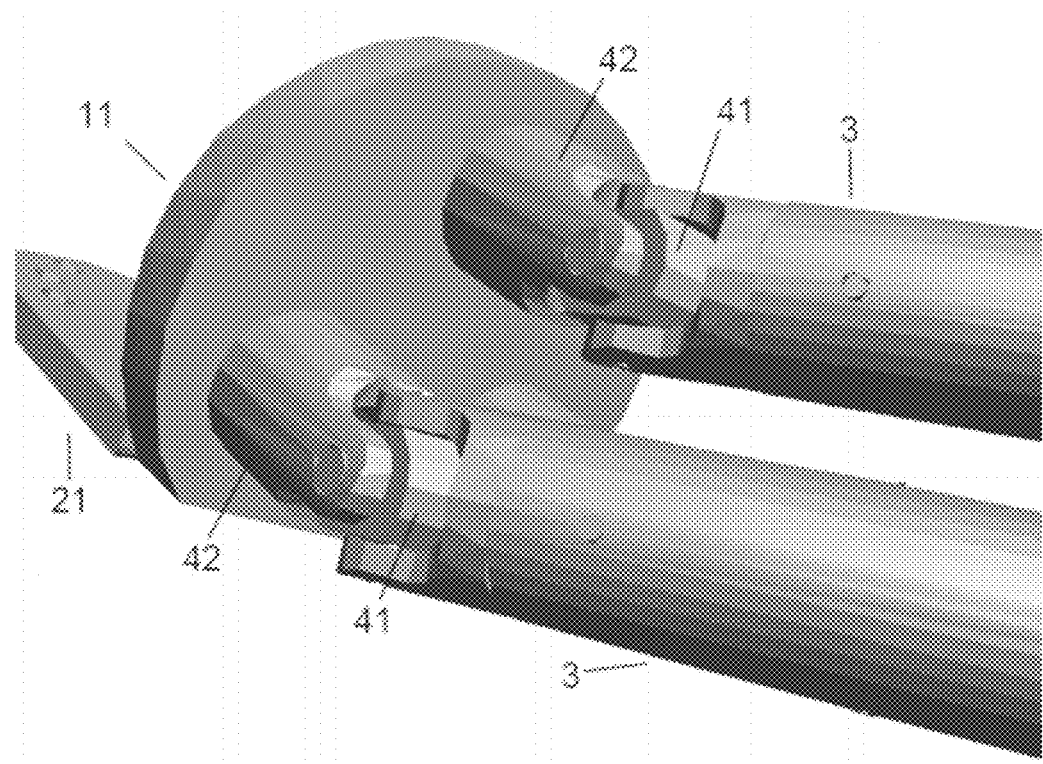
FIG. 5 shows a close-up of two of the universal joints.

FIG. 5 shows a close-up of two of the universal joints 4. In this embodiment, the joints are Cardan joints attaching each rod 3 to a turret 42 extending from the plate. In this embodiment, the rod 3 and turret 42 are hingedly attached to a central gimbal 41, with the two hinges capable of swinging perpendicular to each other. Each joint 4 includes two such hinges and gimbal 41. Behind the turret 42, both the plate 11 and the platform 21 can be seen. In this embodiment, the Cardan joint 4 allows the rod 3 to rotate relative to the turret 42 in the plane defined by the platform 21, while the other hinge allows the rod 3 to rotate relative to the turret 42 in a plane perpendicular to both the plate 11 and the platform 21. In the embodiment shown in the figures, all six Cardan joints 4 are shown with this same orientation, in which each joint 4 contains a hinge that allows only rotation of the attached rod 3 relative to the turret 42 in the plane of the platform 21, 22 to which the turret 42 is attached by way of the plate 11, 12. While this is the only orientation shown in the figures, any orientation of the hinges of the Cardan joints 4 relative to the plates 11, 12 and/or platforms 21, 22 is possible, and the orientation of the joints 4 need not even be the same as each other.

Figure 5A:
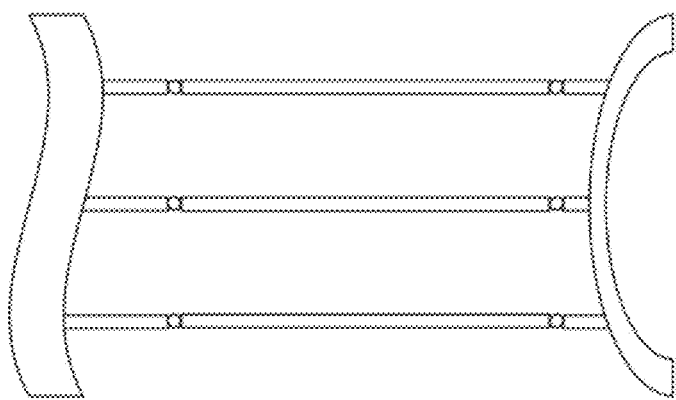
FIG. 5A schematically shows an embodiment of the device having turrets of different lengths.

The turrets may have lengths different from one another, so as to extend between a joint plane and the plate surface, if the plate surface is not parallel to the joint plane. FIG. 5A schematically illustrates an embodiment with turrets of different lengths from one another. The joints lie in parallel planes, so the device will operate as disclosed.

Although not depicted, universal joints other than Cardan joints may be used to connect the rods 3 to the plates 11, 12, for example, Rzeppa joints (see e.g., U.S. Pat. No. 1,665,280), Thomson couplings (see U.S. Pat. No. 7,144,326), tripod joints (see e.g., U.S. Pat. No. 3,757,534) and various other constant velocity joints.

Figure 6:
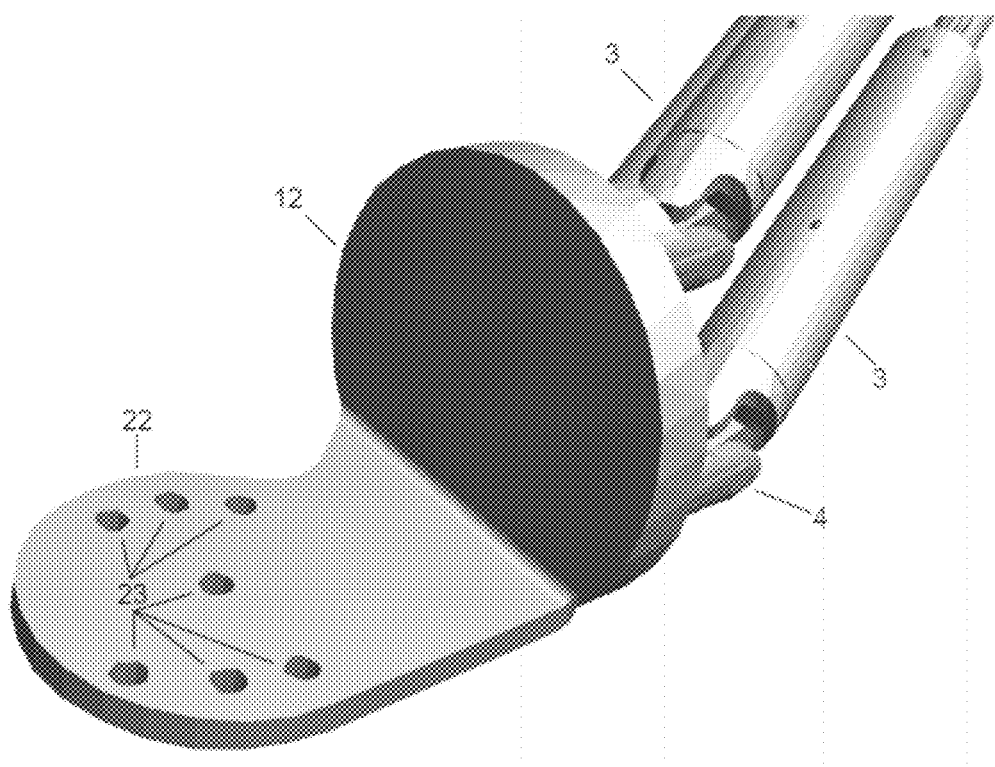
FIG. 6 shows a plate integrally formed with a platform.

FIG. 6 shows the plate 12 and the platform 22 integrally formed. In this embodiment, the platform 22 defines through holes 23 in order to allow attachment of something to the platform 22, for example shoes for human feet, or receptacles for such shoes.

Figure 7:
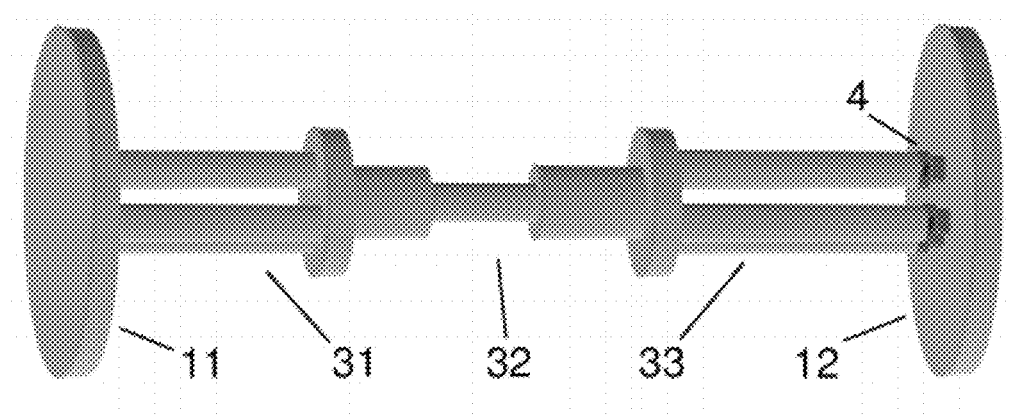
FIG. 7 shows another embodiment that permits dynamic adjustment of plate separation distance.

FIG. 7 shows an alternative embodiment in which the length of the linkage system connecting the two plates 11,12 has dynamically adjustable length, i.e., can be adjusted during normal operation of the device. In this embodiment, the linkage system includes a first set of fixed-length rods 31 attached to first plate 11 by universal joints 4 (not shown), a second set of fixed-length rods 33 attached to second plate 12 by universal joints 4, and an adjustable-length connector 32 to which rod sets 31 and 33 are attached or with which they are integrally formed. In this embodiment, no point on the first plate necessarily remains at a fixed distance from some point on the other plate. The plates are capable of translating relative to each other and incapable of rotating relative to each other (again, minute clearance for articulation in the joints will allow very slight relative rotation, but the plates are still considered to be incapable of relative rotation). Thus in this embodiment, the plates may translate directly toward and away from another, in addition to superior/inferior and anterior/posterior relative translation, thereby allowing the plates to reach all possible positions within the size constraints of the device. The embodiment of FIG. 1 could also permit dynamically adjustable length; in order to permit translation while preventing relative rotation, it should further include a limiter that constrains the three rods to lengthen and shorten together.

The various joints in the disclosed embodiments may be actuated by motors. A control system coupled to the motors may control their actuation. Sensors may be positioned relative to various joints to sense their position, angular relationship between the rods joined by the joint, and/or torque. Sensor data may be transmitted to the control system to permit monitoring and/or to support various control regimes. Examples of control regimes include position control (in which the control system actuates the motors in order to achieve a commanded position; sensors may be used to confirm that the goal position has been achieved and/or halt if unsafe or excessive resistance to further movement is detected), impedance control (in which the control system actuates the motors in order to achieve a commanded apparent mechanical impedance of the device), and admittance control (in which the control system actuates the motors in order to achieve a commanded apparent mechanical admittance of the device).

One exemplary use for the disclosed devices is in treating clubfoot. After a clubfoot deformity has been corrected, for example by the Ponseti method of successive casting, it is possible for the patient to relapse and for the foot or feet to become deformed again. To avoid relapse, the patient's feet may be held in a preferred orientation relative to one another. The embodiment shown in the figures can be used to achieve this goal. By attaching a pair of shoes to the device, one attached to each plate, and putting the patient's feet in the shoes, a correct orientation of the patient's feet may be maintained. Although the patient is allowed to move his feet relative to each other translationally, the patient's feet cannot rotate relative to one another and thus the feet maintain the correct relative orientation. At certain stages of treatment it may be preferable for the patient to wear the device constantly, while in other stages of treatment the patient may wear the device intermittently, for example overnight but not during the day, or vice versa.

Another use for the disclosed devices is to replicate translations of one plate at the other plate. The original and replicated motions would be radially symmetrical to one another about a central point of the device (i.e., the replicated motion would be an inverted minor-image of the original motion), but the motion would be replicated at a distance with high fidelity.

Motorized systems can be used, for example, to automate tasks. If supplied with sensors and a control system, a motorized device could be used to provide gait training, muscle or coordination training, rehabilitation, and the like. A motorized device in which the rods have dynamically adjustable length could be employed, for example, as a boom lift ("cherry picker").

Example

A prototype clubfoot treatment device was built in accordance with the embodiment shown in FIGS. 1-5 and 6-7.

Figure 8:
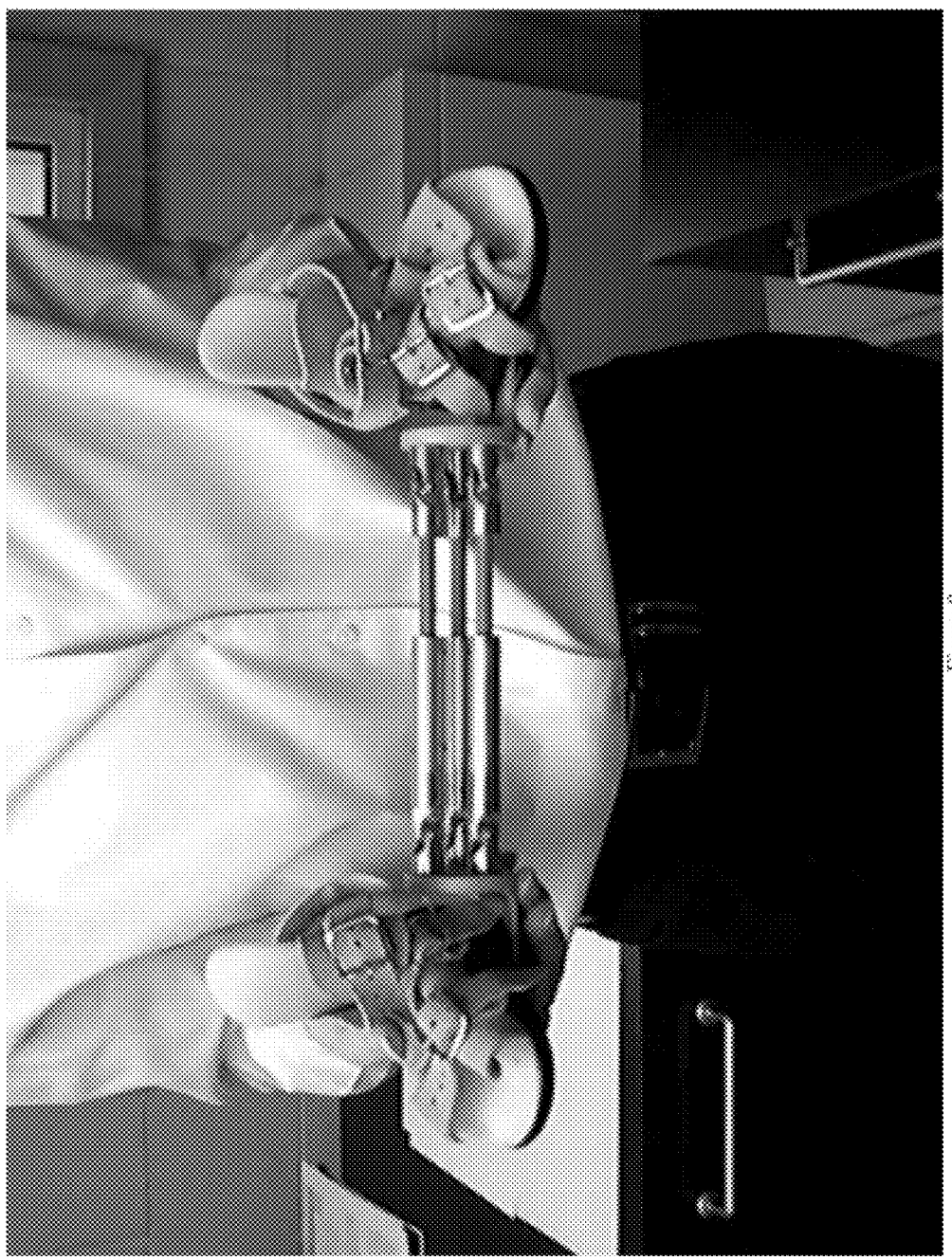
FIGS. 8-46 are sequential still images from a video showing motion of a device prototype.
Figure 9:
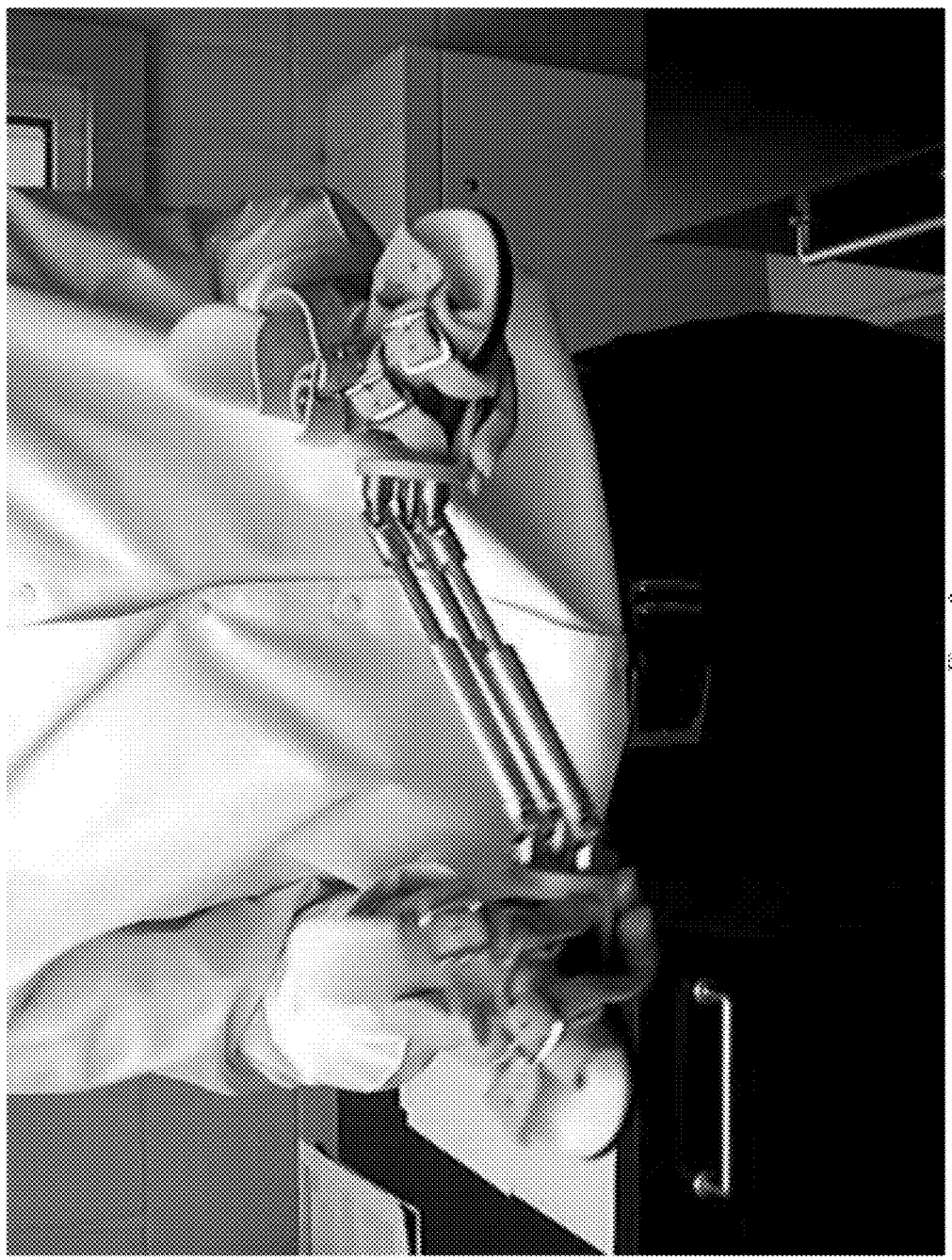
Figure 10:
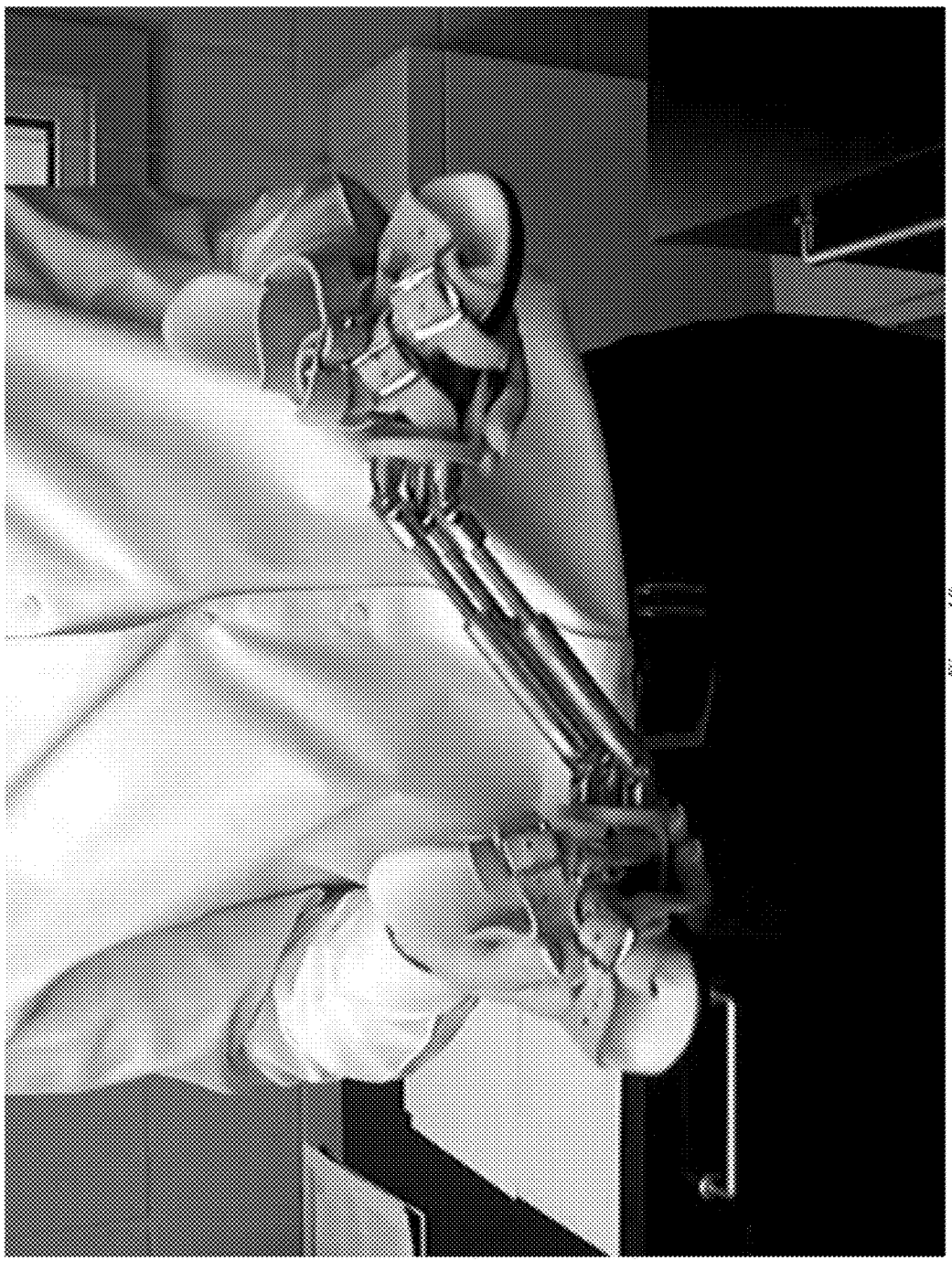
Figure 11:
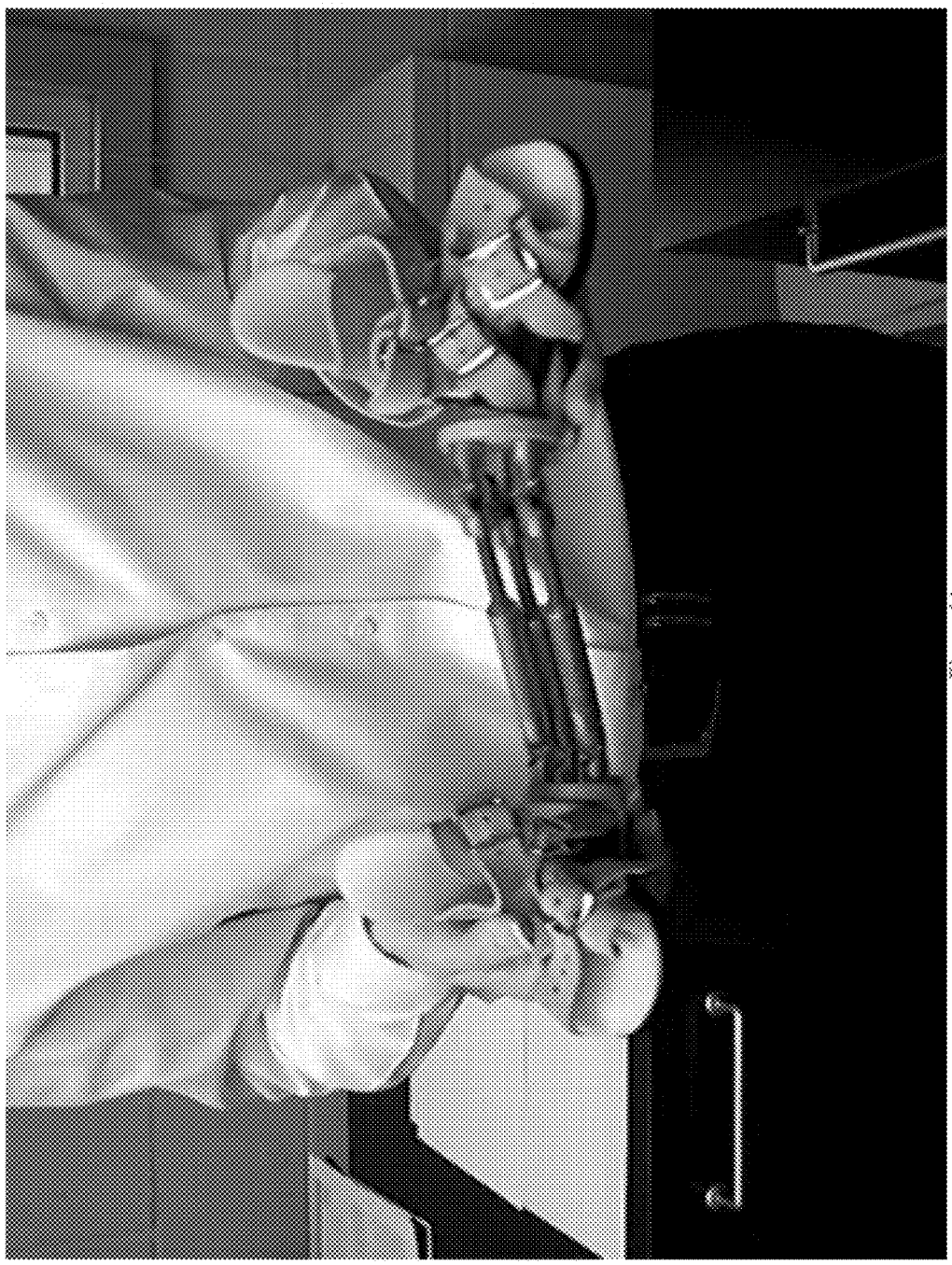
Figure 12:
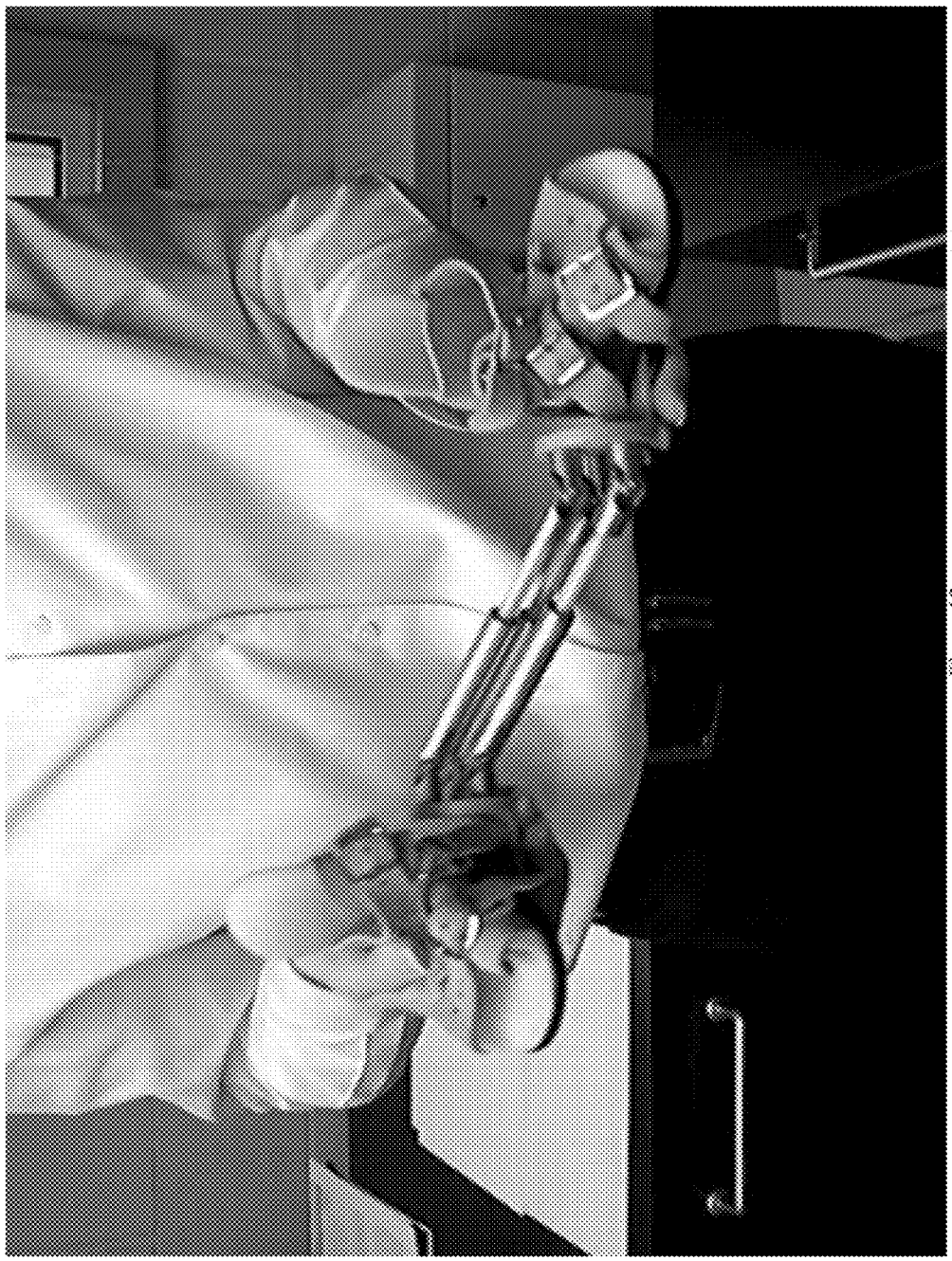
Figure 13:
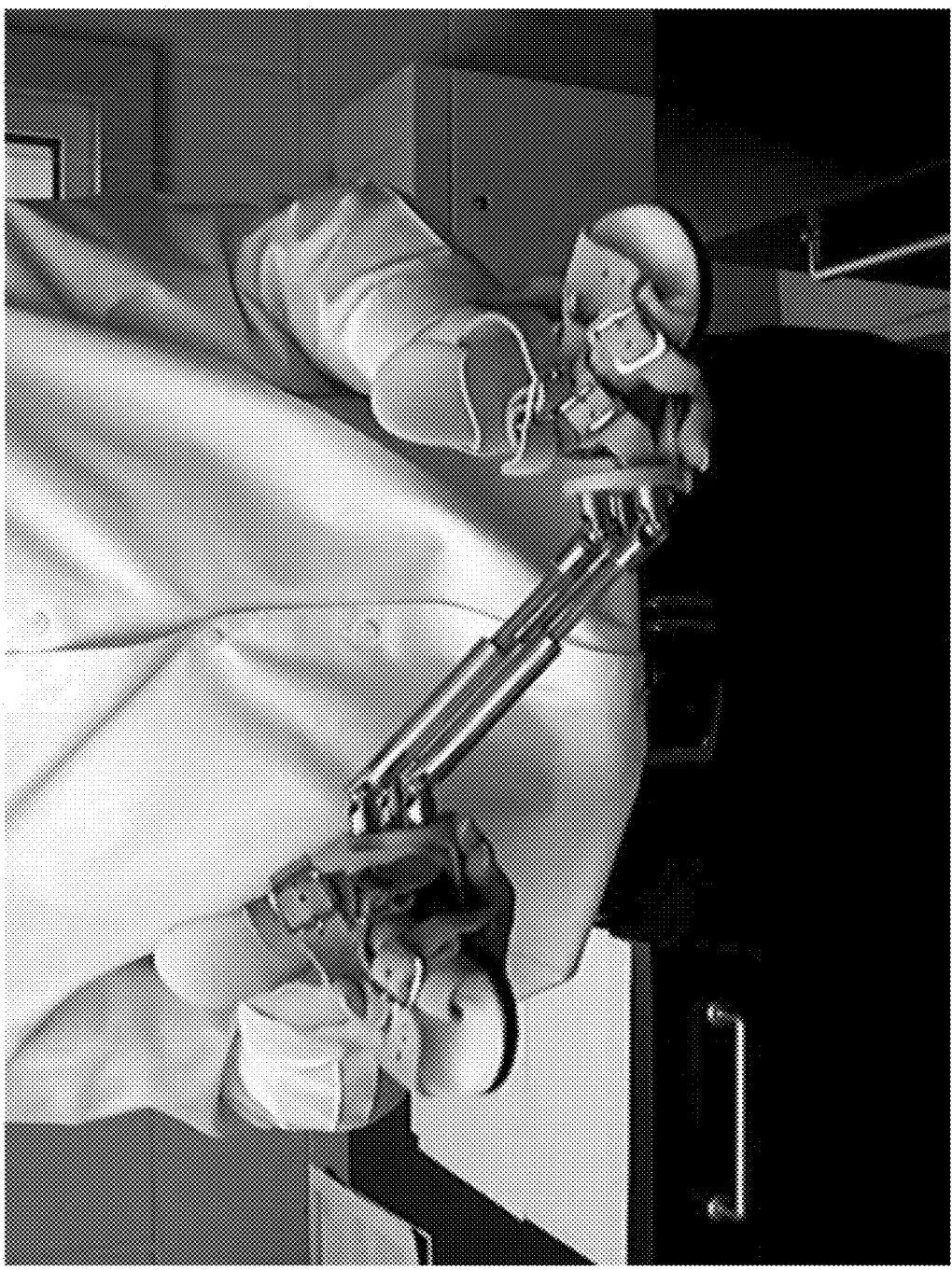
Figure 14:
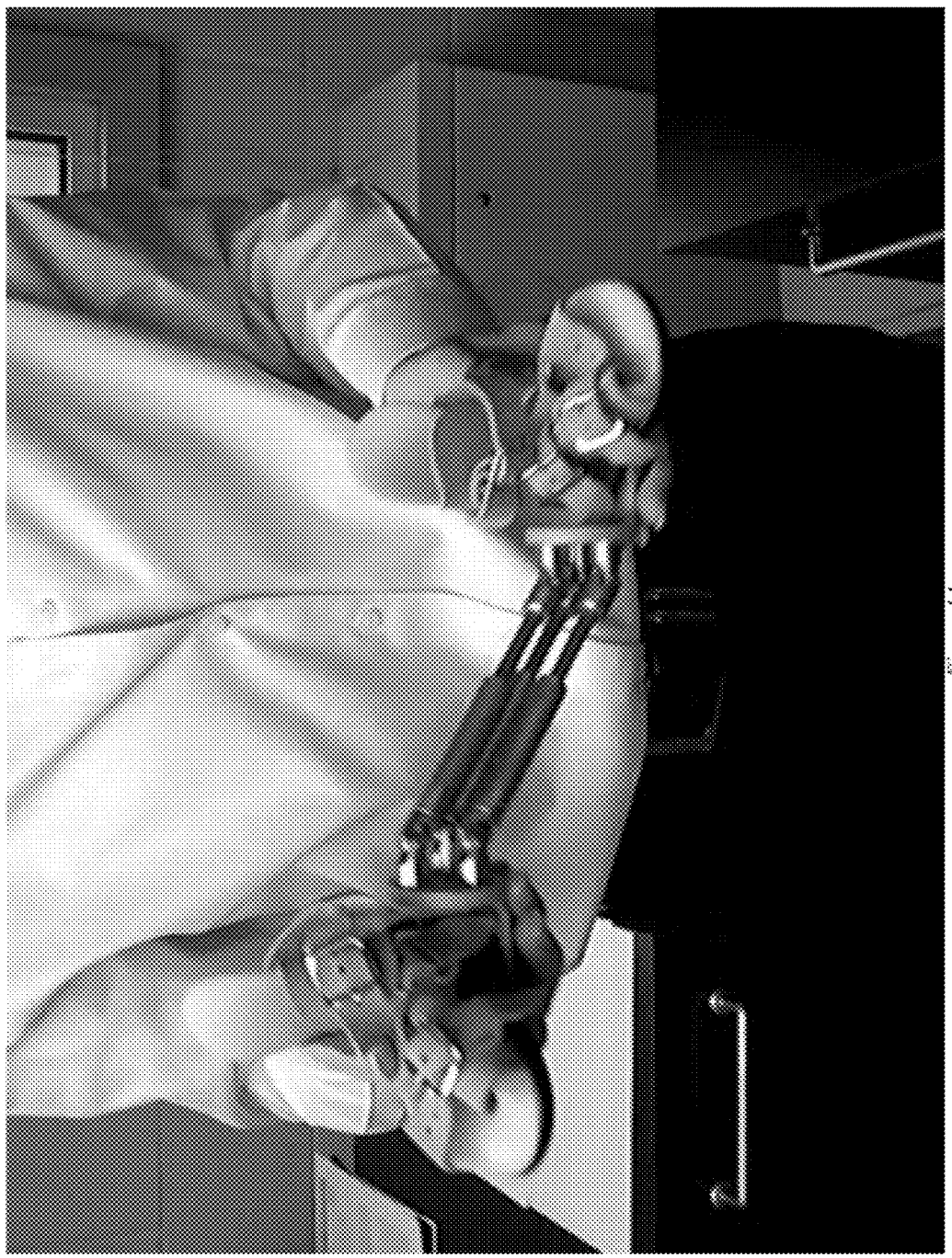
Figure 15:
Figure 16:
Figure 17:
Figure 18:
Figure 19:
Figure 20:
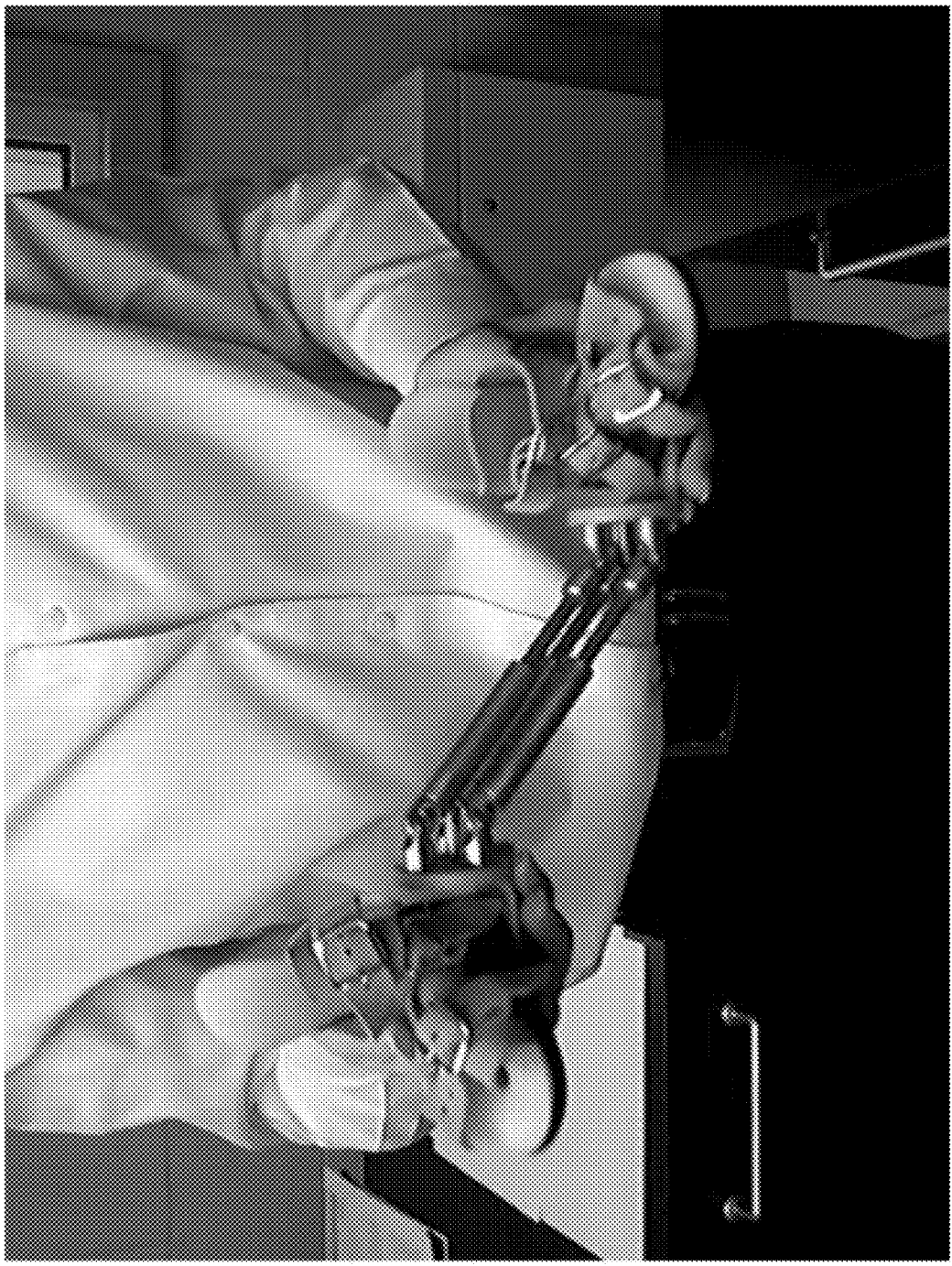
Figure 21:
Figure 22:
Figure 23:
Figure 24:
Figure 25:
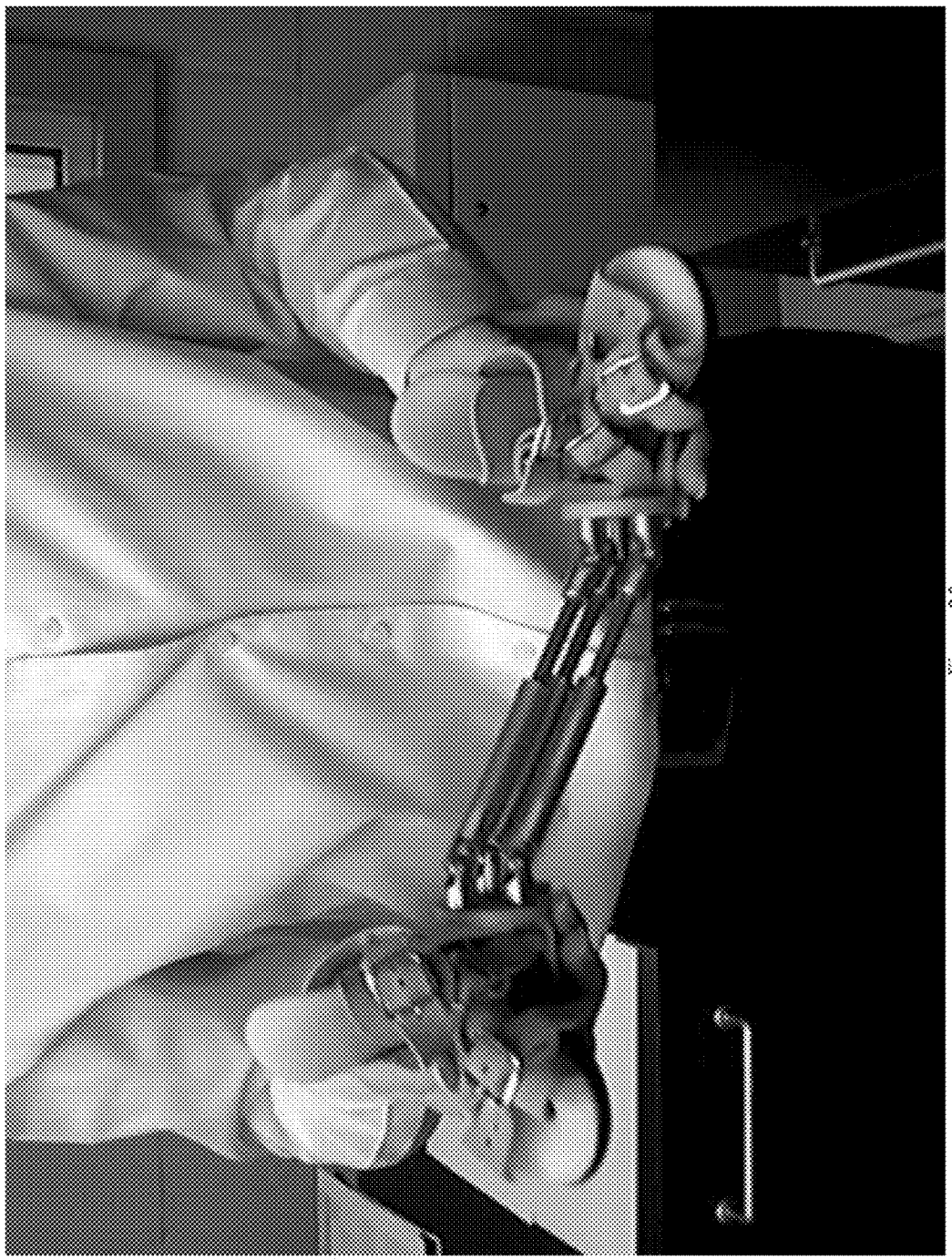
Figure 26:
Figure 27:
Figure 28:
Figure 29:
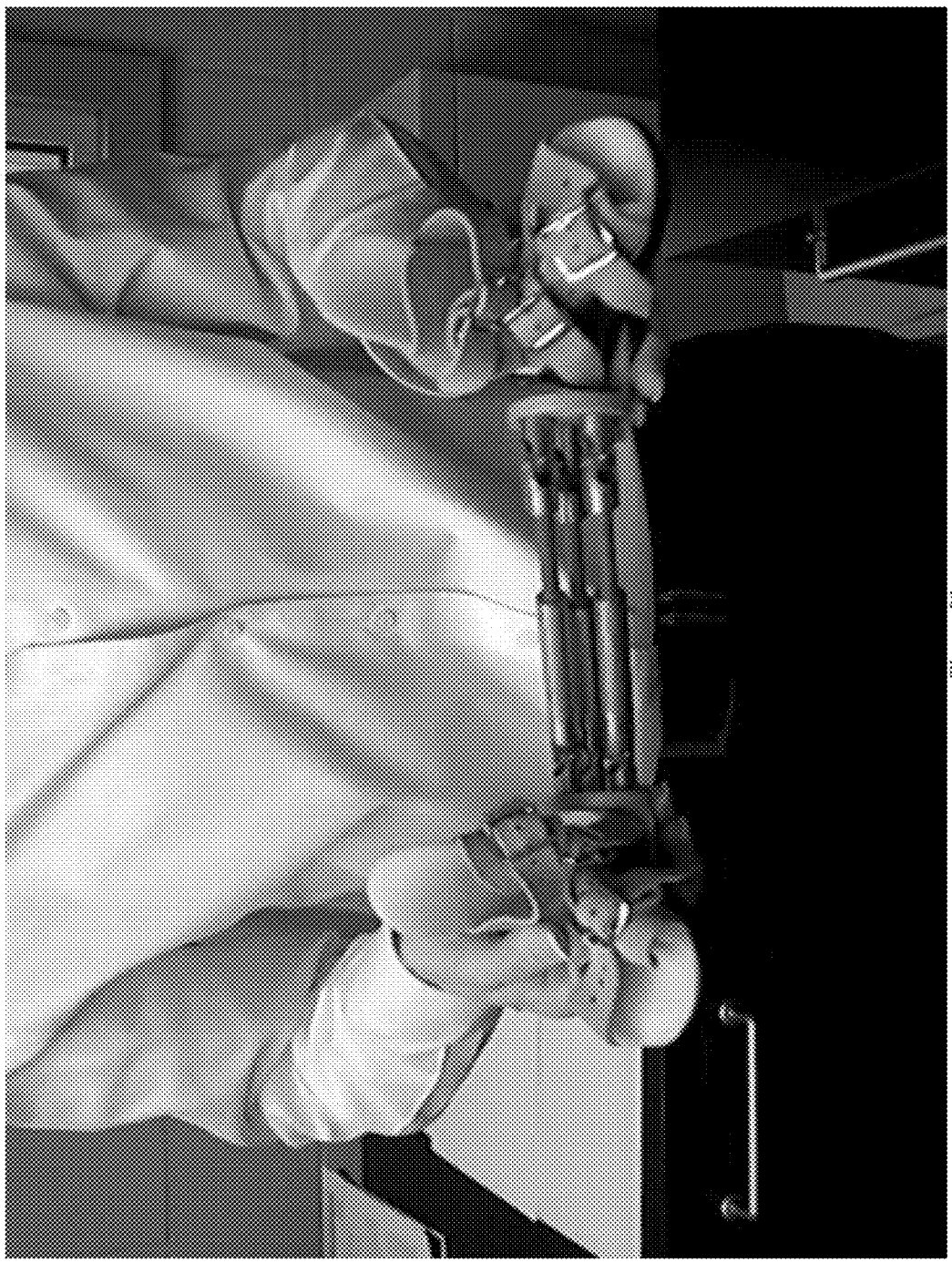
Figure 30:
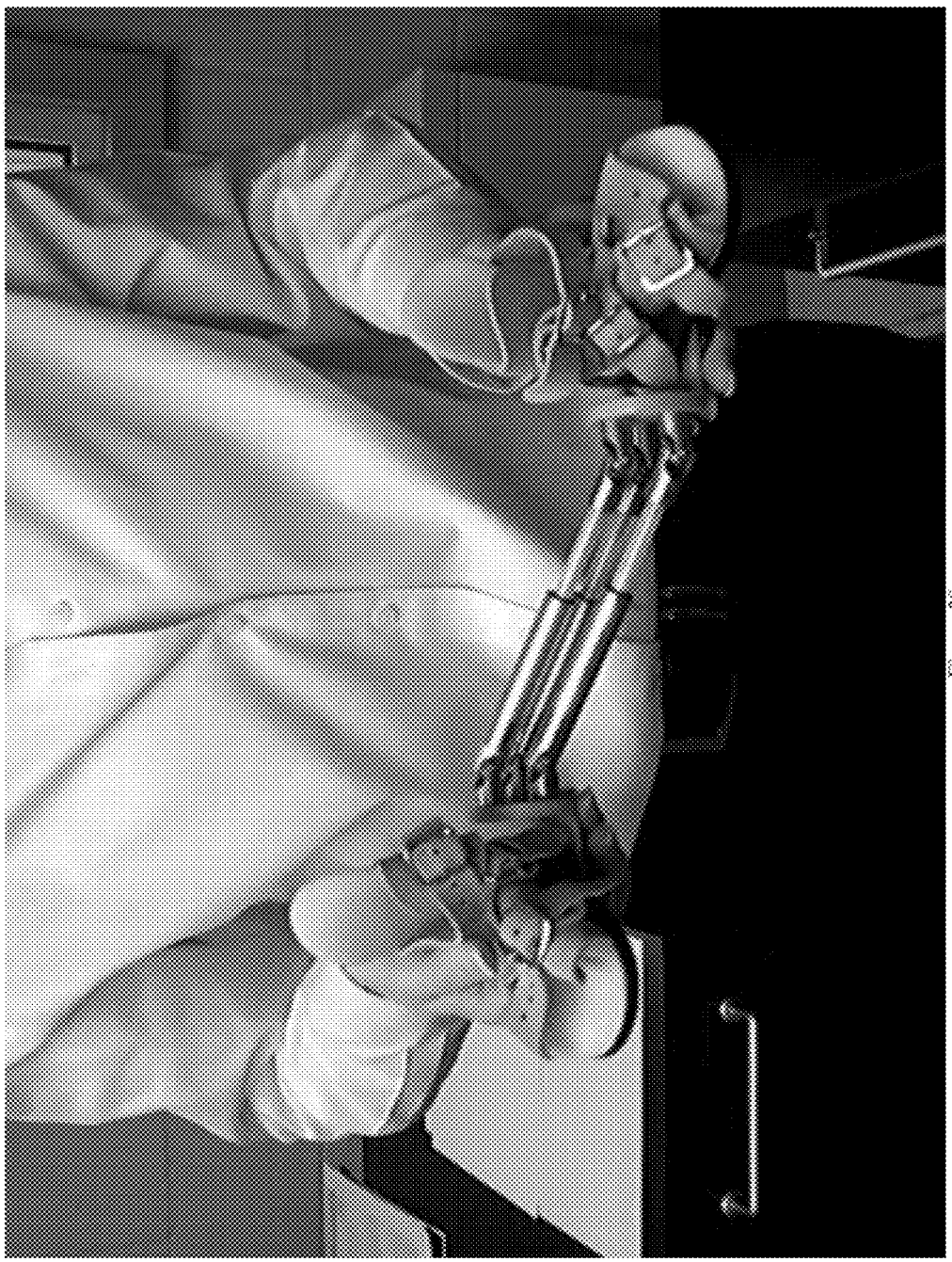
Figure 31:
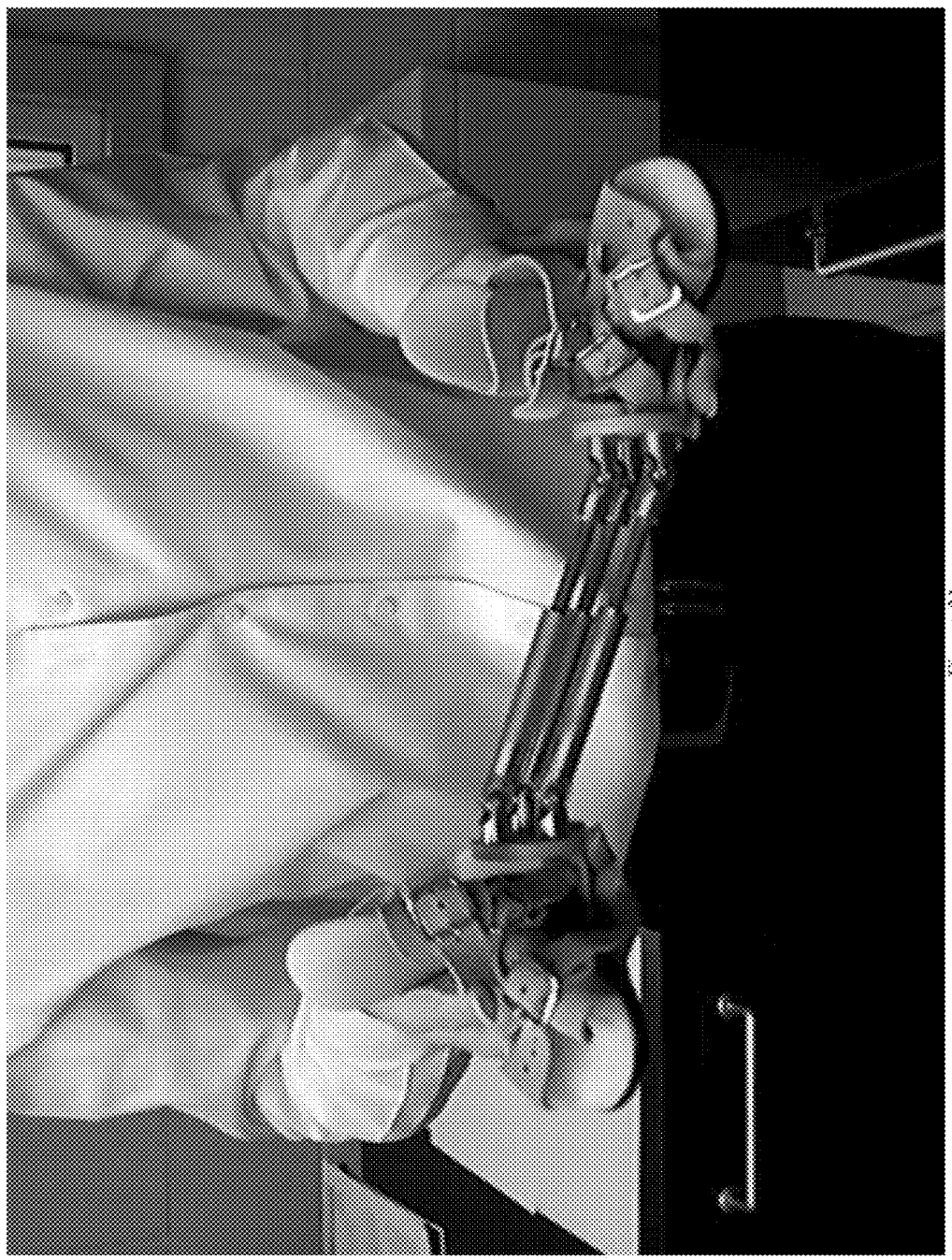
Figure 32:
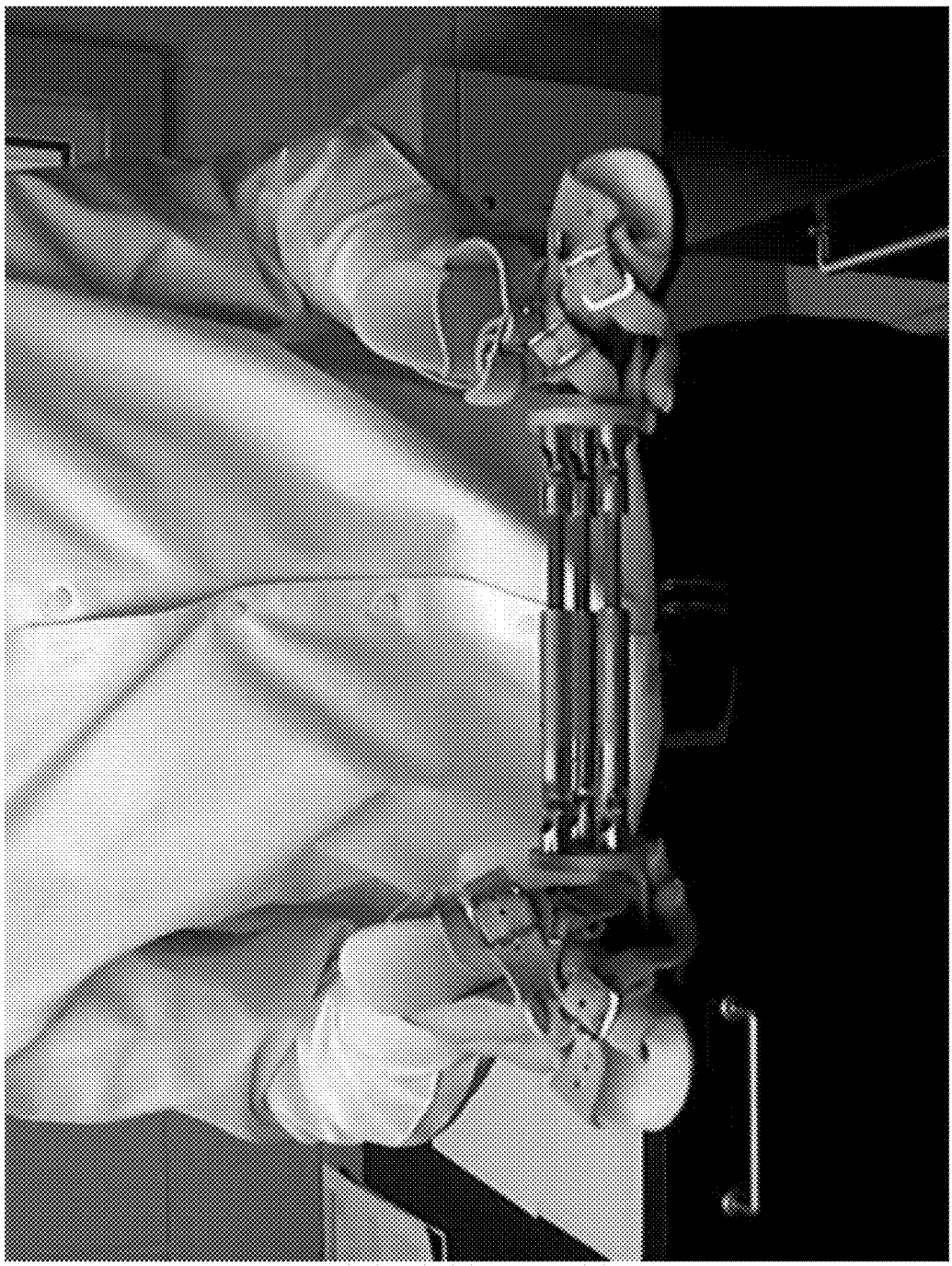
Figure 33:
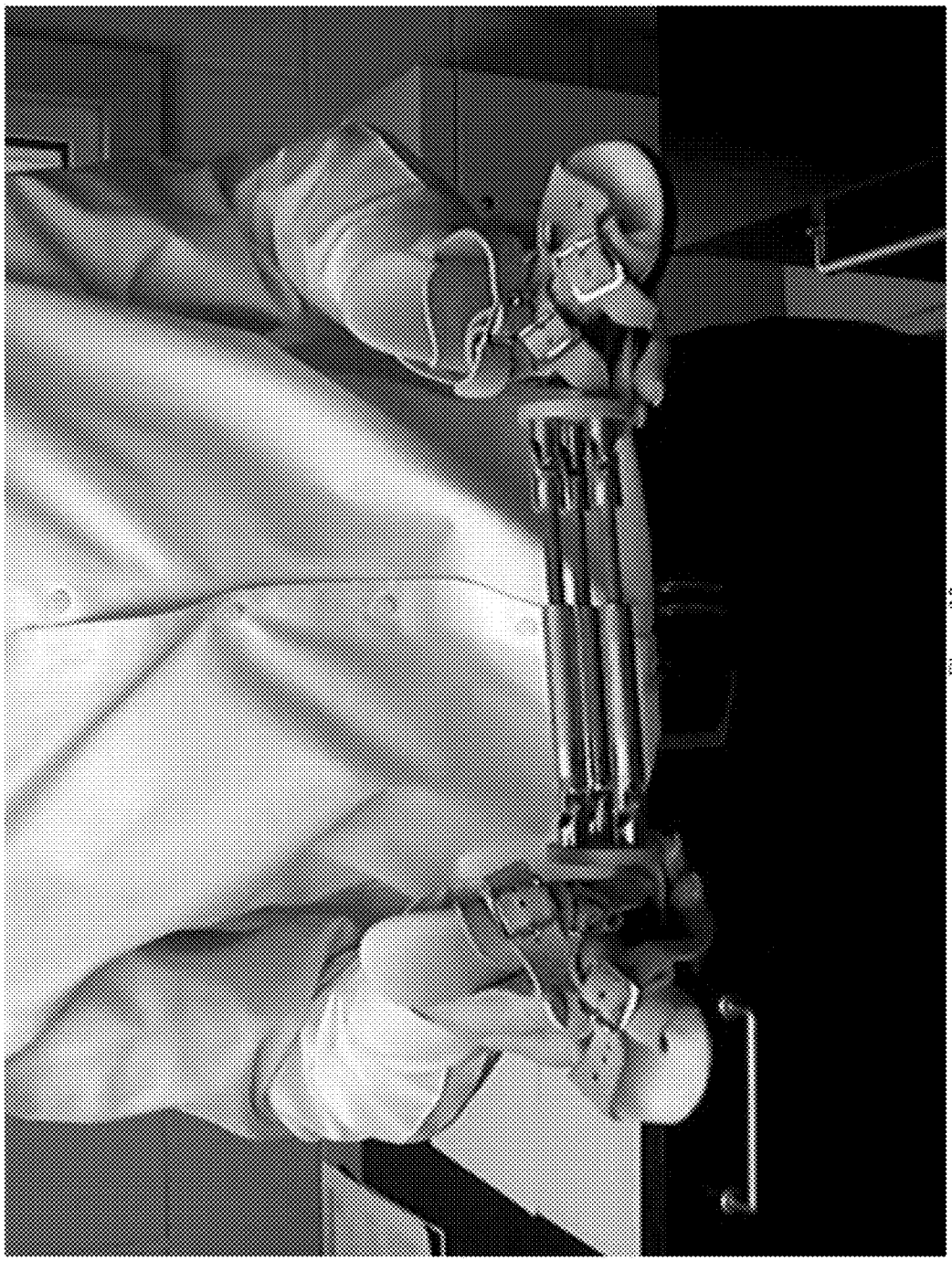
Figure 34:
Figure 35:
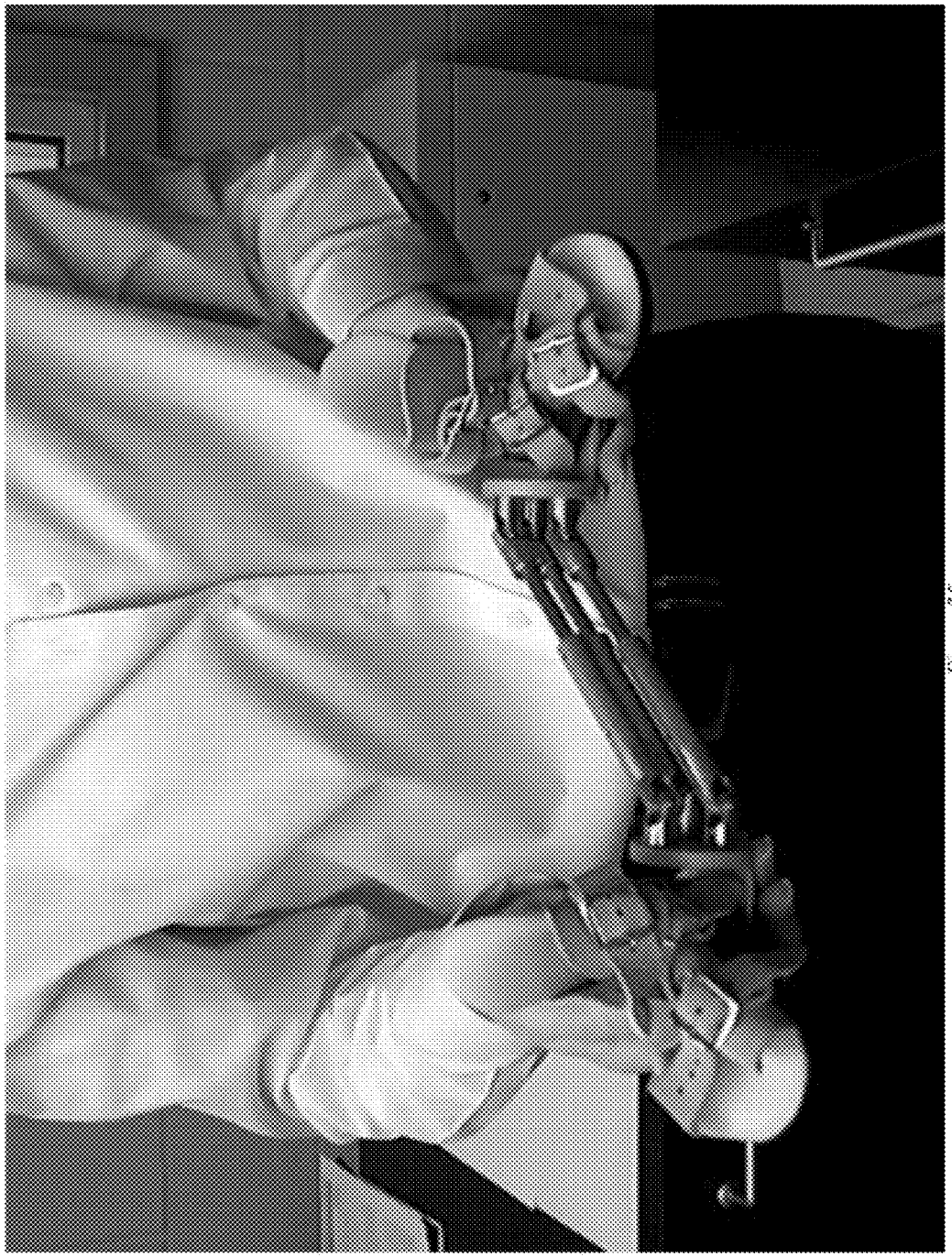
Figure 36:
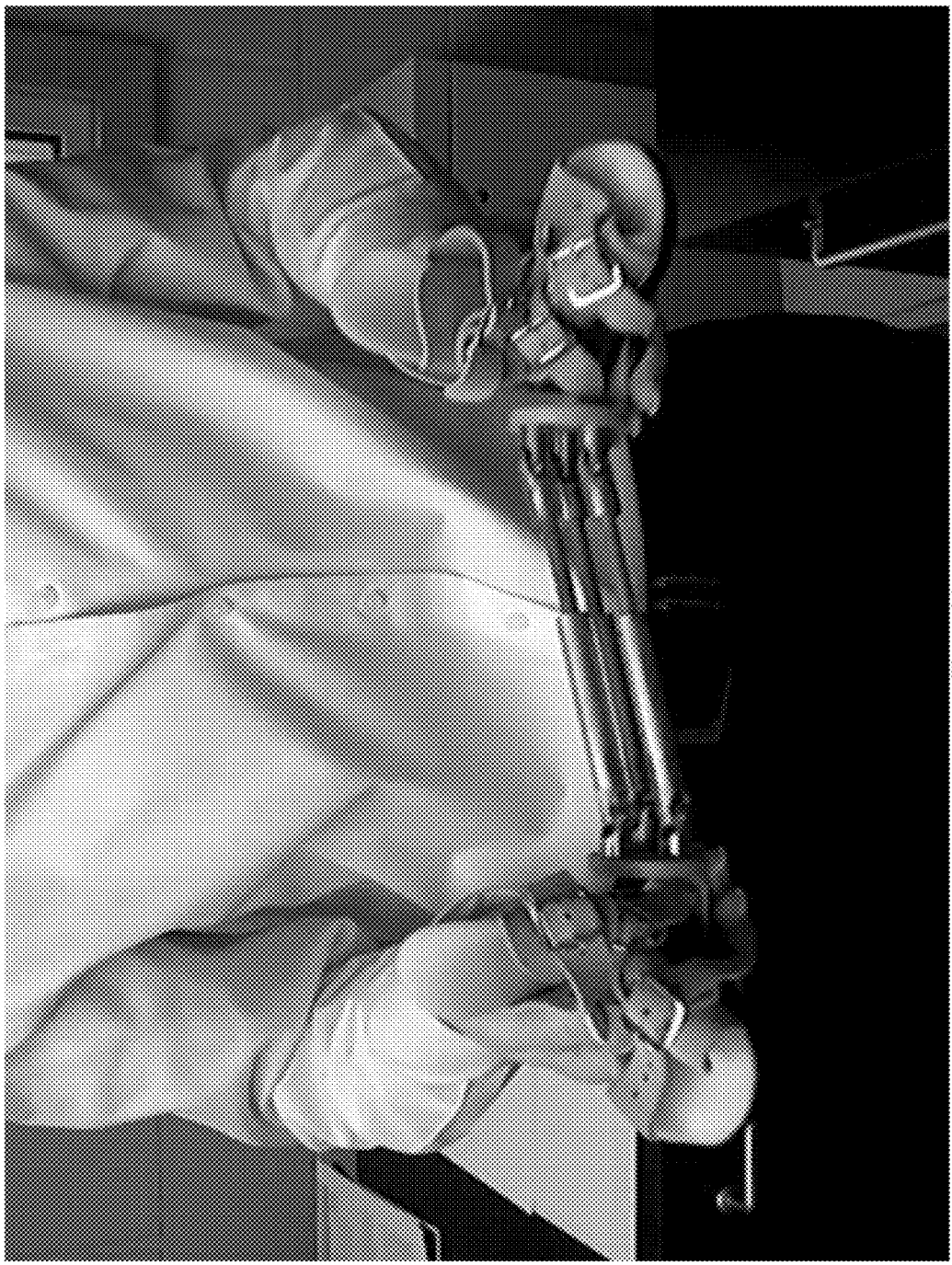
Figure 37:
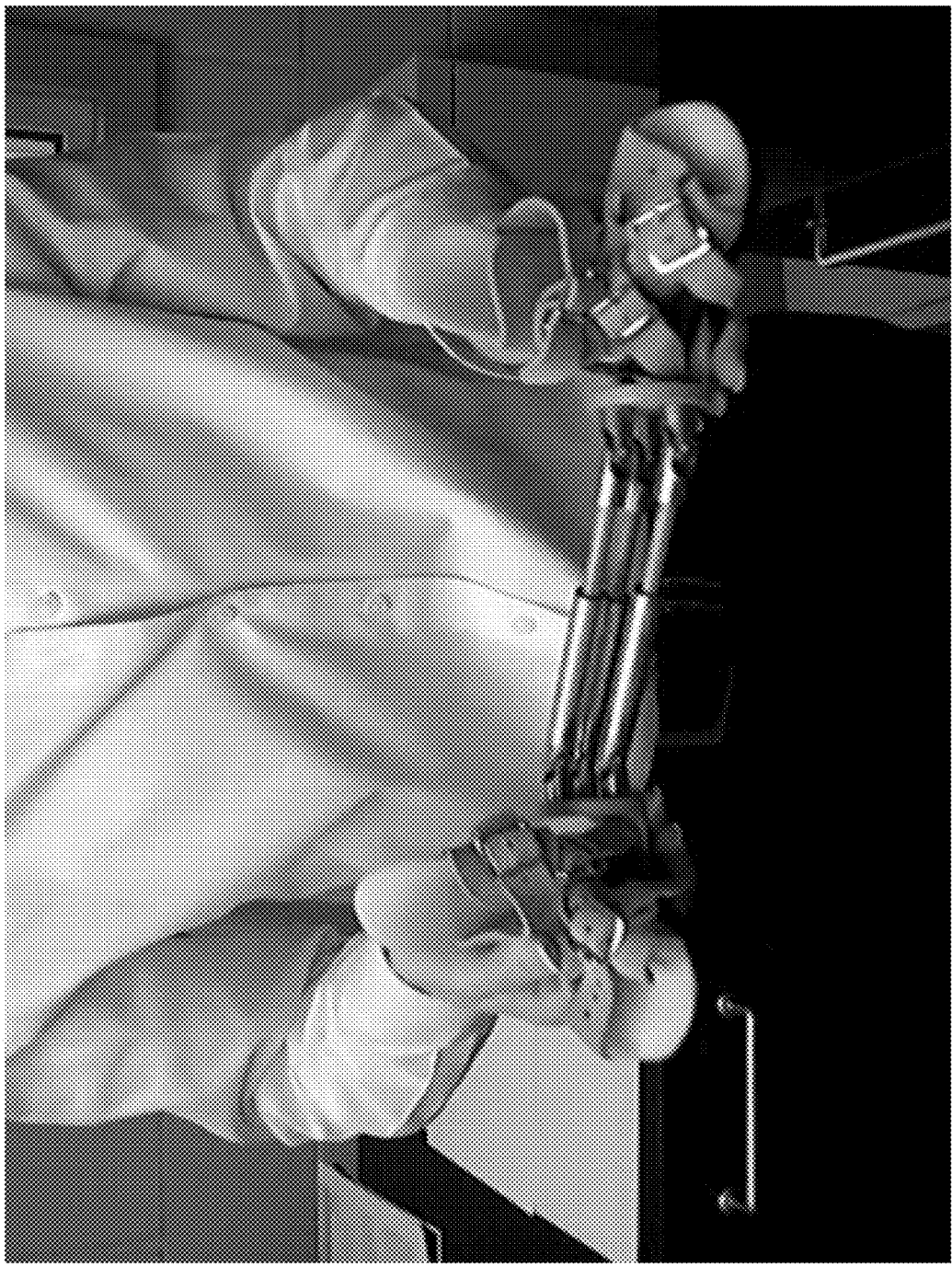
Figure 38:
Figure 39:
Figure 40:
Figure 41:
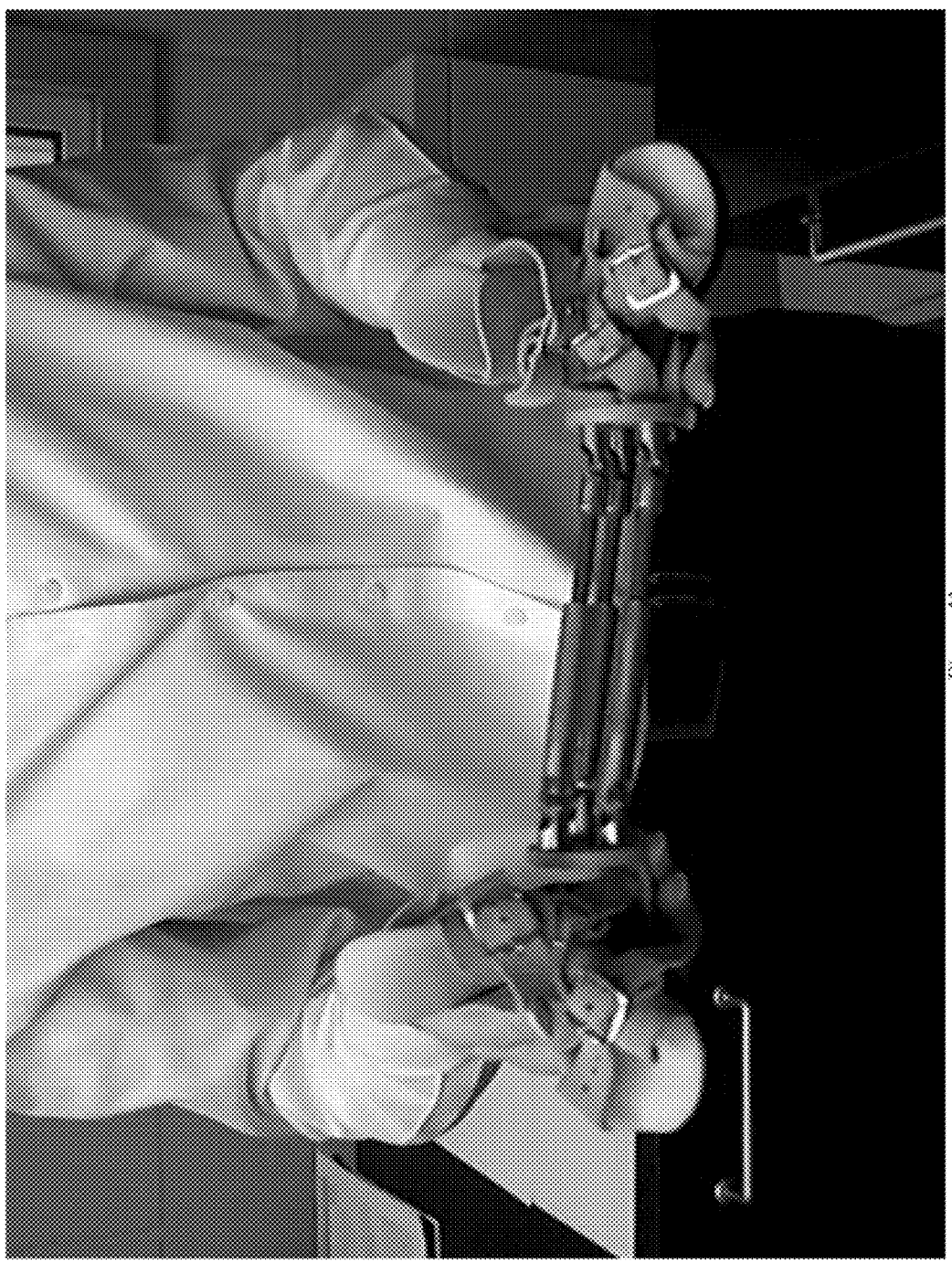
Figure 42:
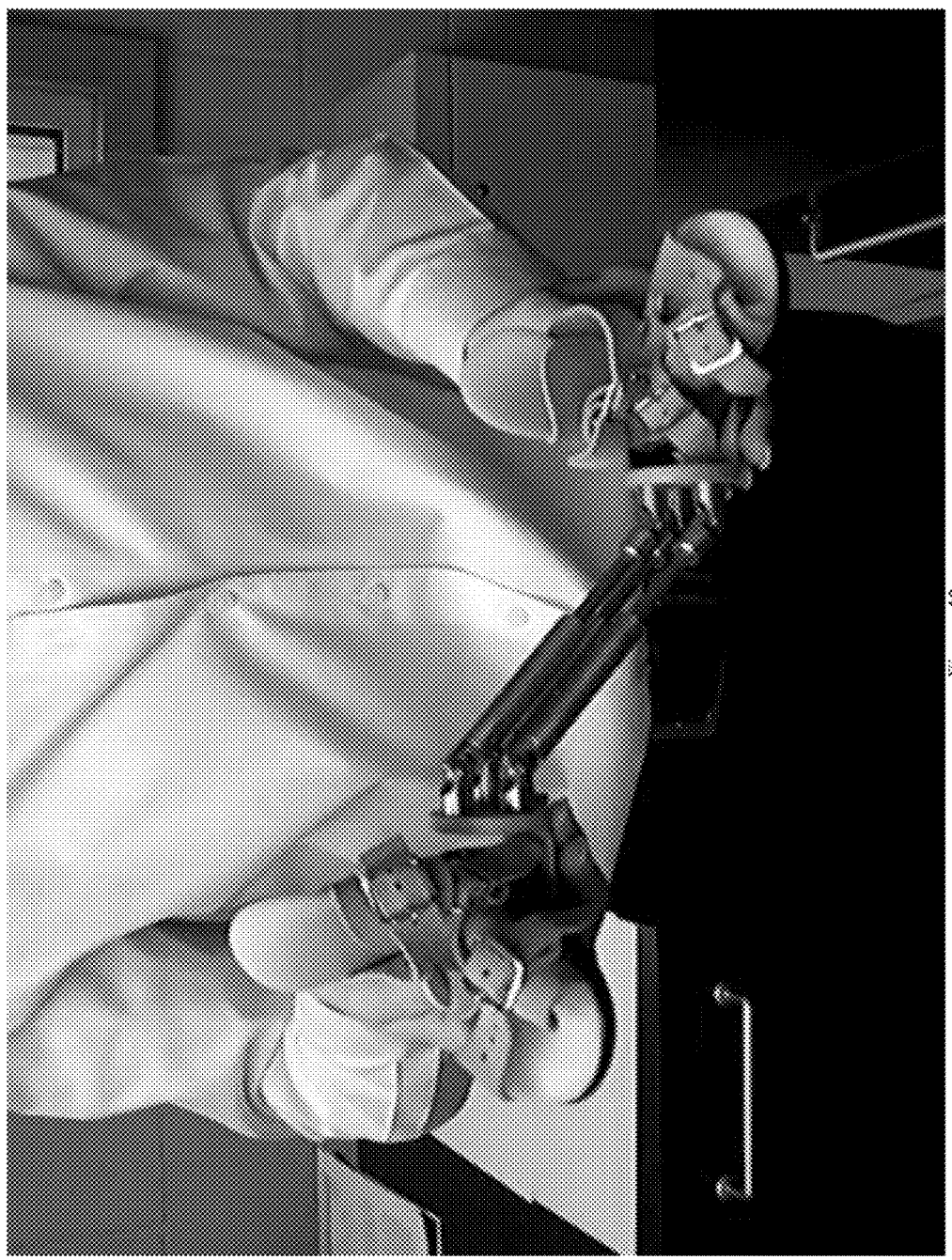
Figure 43:
Figure 44:
Figure 45:
Figure 46:

Shoes were bolted to the platforms with the toes pointing about 70 degrees away from one another. FIGS. 8-46 are sequential still images from a video showing motion of this prototype to illustrate the constrained motions that the device permits. FIGS. 8, 32, and 46 show the neutral position. FIGS. 9-31 show the prototype in a "pedal" motion of diminishing magnitude. FIGS. 33-40 show the prototype in a "shuffling" motion. FIGS. 41-45 show the prototype in a "marching" motion. Note that throughout the demonstrated motions the attached shoes translate relative to one another but do not rotate relative to one another.

We claim:

1. A device comprising
   a first plate and a second plate; and
   a linkage system comprising at least three rods, each having a first end and a second end;
   wherein:
     the first ends of the rods are attached to the first plate, each by a universal joint;
     the second ends of the rods are attached to the second plate, each by a universal joint;
     the rods are arranged such that they are:
       parallel to one another; and
       do not all lie in one plane;
     the universal joints attaching the first plate to the first ends of the rods lie in a first plane; and
     the universal joints attaching the second plate to the second ends of the rods lie in a second plane parallel to the first plane;
   such that:
     the first plate and the second plate are capable of translating relative to each other; and
     the first plate and the second plate are incapable of rotating relative to each other.

2. The device of claim 1 further comprising a first platform attached to the first plate and a second platform attached to the second plate.

3. The device of claim 2 wherein the first plate and the first platform are integrally formed, and the second plate and the second platform are integrally formed.

4. The device of claim 2 wherein the plates are parallel to one another.

5. The device of claim 1 wherein each plate is configured to receive a shoe, each shoe being so sized and shaped as to conform to a human foot.

6. The device of claim 5 wherein each shoe can be rotationally and translationally fixed relative to the plate configured to receive the shoe.

7. The device of claim 1 wherein the three rods are adjustable in length.

8. The device of claim 7 wherein the three rods are capable of assuming a locked state and an unlocked state;
   where in the locked state the lengths of the rods cannot be adjusted; and
   where in the unlocked state, the lengths of the rods can be adjusted.

9. The device of claim 1, further comprising at least one motor actuating at least one joint.

10. The device of claim 9, further comprising at least one sensor monitoring position, angle, or torque of a joint.

11. The device of claim 10, further comprising a control system that receives input from the sensor and actuates the motor.

12. The device of claim 1, wherein a point on the first plate remains at a fixed distance from a point on the second plate in all permitted translations.

13. A method of treating clubfoot in a patient comprising seating the patient's feet in shoes attached to the device of claim 6.

* * * * *